(12) United States Patent
Hayakawa et al.

(10) Patent No.: US 10,087,496 B2
(45) Date of Patent: Oct. 2, 2018

(54) GREEN ALGA LIPID-ACCUMULATING VARIANT AND USE OF THE SAME

(71) Applicants: DENSO CORPORATION, Kariya, Aichi-pref. (JP); Chuo University, Hachioji-shi, Tokyo (JP)

(72) Inventors: Jumpei Hayakawa, Hachioji (JP); Yoko Ide, Hachioji (JP); Shigeaki Harayama, Hachioji (JP); Hidehiko Yasui, Kariya (JP)

(73) Assignee: DENSO CORPORATION, Kariya, Aichi-pref. (JP)

( * ) Notice: Subject to any disclaimer, the term of this patent is extended or adjusted under 35 U.S.C. 154(b) by 0 days.

(21) Appl. No.: 15/037,026

(22) PCT Filed: Nov. 7, 2014

(86) PCT No.: PCT/JP2014/005594
§ 371 (c)(1),
(2) Date: May 16, 2016

(87) PCT Pub. No.: WO2015/075881
PCT Pub. Date: May 28, 2015

(65) Prior Publication Data
US 2016/0273061 A1    Sep. 22, 2016

(30) Foreign Application Priority Data

Nov. 19, 2013 (JP) ................................ 2013-239167

(51) Int. Cl.
| | | |
|---|---|---|
| *C12N 1/12* | (2006.01) | |
| *C12N 9/12* | (2006.01) | |
| *C12N 15/01* | (2006.01) | |
| *C12P 7/64* | (2006.01) | |
| *C12R 1/89* | (2006.01) | |

(52) U.S. Cl.
CPC .............. *C12R 1/89* (2013.01); *C12N 1/12* (2013.01); *C12N 9/1205* (2013.01); *C12N 15/01* (2013.01); *C12P 7/649* (2013.01); *C12P 7/6463* (2013.01); *Y02E 50/13* (2013.01)

(58) Field of Classification Search
None
See application file for complete search history.

(56) References Cited

U.S. PATENT DOCUMENTS

| | | | |
|---|---|---|---|
| 2009/0215140 A1 | 8/2009 | Kurano et al. | |
| 2013/0273620 A1* | 10/2013 | Franz ............... | C12N 1/12 435/134 |
| 2015/0337255 A1 | 11/2015 | Kurata et al. | |
| 2017/0058254 A1* | 3/2017 | Schulz-Raffelt ........ | C12P 19/04 |

FOREIGN PATENT DOCUMENTS

| | | | | |
|---|---|---|---|---|
| EP | 2942390 A1 * | 11/2015 | ............. | C12P 19/04 |
| JP | 4748154 B2 | 8/2011 | | |
| JP | 2013090598 A | 5/2013 | | |
| JP | 2013102715 A | 5/2013 | | |
| JP | 2013102748 A | 5/2013 | | |
| JP | 2014117202 A | 6/2014 | | |
| JP | 6088375 B2 | 3/2017 | | |
| WO | WO-2006109588 A1 | 10/2006 | | |

OTHER PUBLICATIONS

Imamura et al., Genetic transformation of *Pseudochoricystis ellipsoidea*, an aliphatic hydrocarbon-producing green alga, J. Gen. Appl. Microbiol., 2012, 58, 1-10.*
Kajikawa et al., Algal Dual-Specificity Tyrosine Phosphorylation-Regulated Kinase, Triacylglycerol Accumulation Regulator1, Regulates Accumulation of Triacylglycerol in Nitrogen or Sulfur Deficiency, Plant Phys., 2015, 168, 752-64.*
Guiry, How many species of algae are there?, J. Phycol., 2012, 48, 1057-63.*
Uniprot, Accession No. A0A061QMK5, 2014, www.uniprot.org.*
Montero et al., Isolation of high-lipid content strains of the marine microalga *Tetraselmis suecica* for biodiesel production by flow cytometry and single-cell sorting, J. Appl. Phycol., 2011, 23, 1053-57.*
Chochois, The involvement of carbohydrate reserves in hydrogen photoproduction by the green alga *Chlamydomonas reinhardtii*, Ph.D. Thesis, Aix Marseille University (France), 2009.*
Cozza et al., Quinalizarin as a potent, selective and cell-permeable inhibitor of protein kinase CK2, Biochem. J., 2009, 421, 387-95.*
Patnaik, Engineering Complex Phenotypes in Industrial Strains, Biotechnol. Prog., 2008, 24, 38-47.*
Kumar et al., Molecular tools for bioengineering eukaryotic microalgae, Current Biotechnol., 2016, 5, 93-108.*
Schulz-Raffelt, Miriam et al., "Hyper-accumulation of starch and oil in a Chlamydomonas mutant affected in a plant-specific DYRK kinase," Biotechnol Biofuels, 9:55, 2016.

(Continued)

*Primary Examiner* — Robert B Mondesi
*Assistant Examiner* — Todd M Epstein
(74) *Attorney, Agent, or Firm* — Harness, Dickey & Pierce, P.L.C.

(57) ABSTRACT

A green alga variant having a dual-specificity tyrosine-phosphorylation regulated protein kinase activity that is reduced compared to a dual-specificity tyrosine-phosphorylation regulated protein kinase activity of a parental strain is provided. The green alga variant increases a total amount of a lipid production per unit time and per unit culture area compared to a total amount of a lipid production of the parental strain. A dual-specificity tyrosine-phosphorylation regulated protein kinase of the parental strain is a protein having an amino acid sequence with at least 50% sequence identity with the amino acid sequence of an active site and a substrate recognition site of SEQ ID NO: 4 and having the dual-specificity tyrosine-phosphorylation regulated protein kinase activity.

5 Claims, 7 Drawing Sheets
Specification includes a Sequence Listing.

(56) References Cited

OTHER PUBLICATIONS

Vincent Chochois, "The involvement of carbohydrate reserves in hydrogen photoproduction by the green alga *Chlamydomonas reinhardtii*", Thesis at the Aix Marseille University Faculty of Science, 2009, 1(141) Abstract.

Yusuf Chisti, "Constraints to commercialization of algal fuels", Journal of Biotechnology, 167(2013) 201-214.

Yuji Nakajima and Ryohei Ueda, "Improvement of photosynthesis in dense microalgal suspension by reduction of light harvesting pigments", Journal of Applied Phycology, 1997, 9:503-510.

Yuji Nakajima and Ryohei Ueda, "The effect of reducing light-harvesting pigments on marine microalgal productivity", Journal of Applied Phycology, 2000, 12:285-290.

Melanie Oey et al., "RNAi Knock-Down of LHCBM1, 2 and 3 Increases Photosynthetic H2 Production Efficiency of the Green Alga *Chlamydomonas reinhardtii*", PLOS One, Apr. 2013, vol. 8, Issue 4, e61735.

Xinyao Liu and Roy Curtiss III, "Nickel-inducible lysis system in *Synechocystis* sp. PCC6803", Proceedings of the National Academy Sciences of the United States of America, Dec. 22, 2009, vol. 106, No. 51, 21550-21554.

Xinyao Liu et al., "Fatty acid production in genetically modified cyanobacteria", Proceedings of the National Academy Sciences of the United States of America, Apr. 26, 2011, vol. 108, No. 17, 6899-6904.

Akira Satoh et al., "Characterization of the lipid accumulation in a new microalgal species, *Pseudochoricystis ellipsoidea* (Trebouxiophyceae)", Journal of the Japan Institute of Energy, 2010, vol. 89, 909-913.

Takuro Ito et al., "Metabolic and morphological changes of an oil accumulating trebouxiophycean alga in nitrogen-deficient conditions". Metabolomics, 2013, 9:S178-S187.

Zi Teng Wang et al., "Algal Lipid Bodies: Stress Induction, Purification, and Biochemical Characterization in Wild-Type and Starchless Chlamydomonas reinhardtii", Eukaryotic Cell, Dec. 2009, vol. 8, No. 12. p. 1856-1868.

Pengcheng Wang et al., "Quantitative phosphorproteomics identifies SnRK2 protein kinase substrates and reveals the effectors of abscisic acid action", Proceedings of the National Academy Sciences of the United States of America, Jul. 2, 2013, vol. 110. No. 27, 11205-11210.

Guillaume Blanc et al., "The genome of the polar eukaryotic microalga *Coccomyxa subellipsoidea* reveals traits of cold adaptation", Genome Biology, 2012, 13:R39 (PMID: 22630137).

Paul A. Broady, "The Morphology, Distribution and Ecology of *Pseudococcomyxa simplex* (Mainx) Fott (Chlorophyta, Chlorellaceae), a Widespread Terrestrial Antarctic Alga", Polar Biology, 1987 7:25-30.

Meera Soundararajan et al., "Structures of Down Syndrome Kinases, DYRKs, Reveal Mechanisms of Kinase Activation and Substrate Recognition", Structure, Jun. 4, 2013, 21:986-996.

Sheng-He Huang, "Inverse Polymerase Chain Reaction: An Efficient Approach to Cloning cDNA Ends", Molecular Biotechnology, 1994, vol. 2, 15-22.

Thomas Gaj et al., "ZFN, TALEN, and CRISPR/Cas-based methods for genome engineering", Trends Biotechnol., Jul. 2013, 31(7): 397-405.

Heriberto Cerutti et al.. "RNA-Mediated Silencing in Algae: Biological Roles and Tools for Analysis of Gene Function", Eukaryotic Cell. Sep. 2011. p 1164-1172.

E.G. Bligh and W.J. Dyer, "A rapid method for total lipid extraction and purification", Canadian Journal of Biochemistry and Physiology, Aug. 1959, vol. 37. No. 8, 911-917.

Database GenBank [online], Accession No. EDP02163, 2007 [Date of Search: Sep. 12, 2017], URL, https://www.ncbi.nlm.nih.gov/protein/158276390?sat=21&satkey=15254748 (3 pages).

Database GenBank [online], Accession No. ED098379, 2007 [Date of Search: Sep. 12, 2017], URL, https://www.ncbi.nlm.nih.gov/protein/158272581?sat=21&21&satkey=15254722 (3 pages).

Database GenBank [online], Accession No. EIE26492, 2012 [Date of Search: Sep. 12, 2017], URL, https://www.ncbi.nlm.nih.gov/protein/EIE26492.1 (3 pages).

\* cited by examiner

IHCDLKPENVLLKGLDSGEIKVIDFGSACFENRTMYSYIQSRFYRSPEVLLGYPYDVAI
DMWSLGCMAAELYLGLPLFPGASE (SEQ ID No:4)

Forward : 5' ATC CAC TGC GAC CTN AAR CCN GAR AA (SEQ ID No:5)
Reverse1: 5'    CA GCC CAR RCT CCA CAT RTC DAT (SEQ ID No:6)
Reverse2: 5'    CA GCC CAR NGA CCA CAT RTC DAT (SEQ ID No:7)

FIG. 6A

```
CATTTCAATCCAAAAAAGAGAAGGATAGAGAGTTGCGAAGATGGTCTGTGCATGCAAGTT
GTTTTGATCACGATGTTGCTGTCATAGGTTGCGAGGTAGAAGTTGCTTCCAGAATATTGC
TTCTCATCATCTGGCTTGTACTTTTGTGTGCATGCTGAGAACATAGCTCTGAAACCGATG
AGTTACCATATGCTCATAATCTGCGCCGATGCATCCTCTGACAGGCAGATTGATCCAAGT
TGGCCAGCCATAGTCTTCTTGAAAGAGAGGAAGAACTGTGCTGTGAAGTTGTTATCTAGC
GGTTGAAGCGATCTGGCTCTAAGGGCACGGATAGACGAGAAGACATCGTTCAAATCCTAG
GTGCGTTGCATATATTTCCCGCTTAGCCTCCCAGGAGCATTTCTAAAACCCAAGATTGTT
CACGACACCAGGCAACACTGATGCTACTTCAACAAGCGTGGGCAATGCCACATTTTGATT
TTCTTGCAGCTGTATCCTCTACGGTGTGATTTCTTCTCATATGTTGGCAGGACGTGCATC
GCCTCAGGTCTGACTCGATGGACAACCAAAGCTCAGGCACCTCCAGGGGCATGGAAAGGA
GGTGTCTGACTGTTCCGGGCTTGGGAAAAGGCAACGAAGGCTTTGACAACGAAAATAACG
ACCTCATATTGTATGTGGATGACGTCCTTTCCGTGAAAGAAAGGAGGTGTGTTGCTTTTC
CTCTCATTTCTGTGCCTGTGAGGATTATACTTGCTCGGCAGACGAGCACCCGCGGCATCT
GAATCTACTCTTAGTTCCACTCATGGTGAGTATTCTTAGTGCTTATTCGACGCTCTTCCT
CATTCACAGGTACATTGTCAGGGATATGCTGGGCCAAGGCACCTTCGGGCAGGTCGTGCG
ATGCCTTCGAGAGGATAGCCGTGAGGAAGTGGCTGTGAAGGTCATTAAGAATCAAACTGC
CTTCTATCATCAGGTCAGTAGGGCATTGAAGGGCGGCTTATTCCCTCGTCCGTGTACTGA    JH1011 (G->A)
TCGTTCTTAGCTTGTTTTCTTCGGCATCCGTTGTCCGAGGGGCCTGCTCGCCGCTGATGG
CATGTGGCTCTGTATAGCCAGTAGTGATGCTAGTCTGTCTATGCAGGCTCGTGTCGAGGT
GGGCGTCCTGCAGTTTCTGAACACCCGGGGGGATCCAGAGAACAGGCATCACATCGTGAG
GATGCGCGACTTCTTTCTGTTCCGTAACCATCTCTGCCTCGTGTTCGAGCTCTTGAGCGT
CAACCTGTACGAGCTCGTCAAGCACAACCAGTTCAGGGGCCTGTCTATGAACCTCCTGCG
CGTTTTCATCAGCCAGGTACAGAAGATCCTAGTGACACAGCACCTGATATTGGGACACTG
CGGCCCTCCAGGCCCCAGTGCACTCACGTGGTGTTGCGCTTGTCTTTGCAGTATATTGTA
GCACTCCTCTGCAGCTTTCTGGATGCTCCCAATTACACCAGTAAGGATATTACCTTCCTC
GCGTCTCCCTCTGTCACCTACTTGTGCAGGGTCATGCACCAACACAGGCGTCTGTGTGTT
TTGACATGTCTAAGATTACAAGCTCGTGTGCTGTTCTGCAGATCTTGGACGCACTGTCAG
TGCTCCATGAATGCAACATTATCCACTGCGATCTCAAGCCGGAGAACGTGCTGCTCAAGG
GACTAGACTCGGGGGAAATCAAAGTCATCGACTTCGGGTCAGCTTGCTTTGAGAATCGCA
CCATGTACTCCTACATCCAGTCACGGTTCTACCGCTCCCCGGAGGTGACCGTCCCAGCAC
TGTCAGACCTTCCAGCCTTTCTAGTATGATTGATCTTCAAGGAAGCACTTCTGGCTGCTG
TCCTTGTGGCATACTTAGTTCATTAATTCCATGCAGCGTCCCACCTCAGTTCTTCCTTTT
TGAAAGACAGCAATCTCAGTGGCTTGAACAGGGTGGAGCAAACTTGGTGTAGAGCACTGC
CTGTTCTCAATGACTGTGCCTGATGGAAGCAGCCATAAGAAACTTGTTTGTGGTGCCAGG
TGCTGCTGGGGTACCCATATGATGTGGCCATTGATATGTGGTCACTGGGCTGCATGGCGG    JH1013 (G->T)
CTGAGCTCTACCTGGGTTTGCCCTTGTTTCCGGGCGCCTCGGAGCACGATCTCCTGGTGC
GCATCGTGGAGATGCTGGGAATGCCTCCACCACATGTGCTGGCACGCGCACAGCACCTGC
GCAAATACTTCAAGCGCGAGGAGGAAGTCCTGAATGTGGGAGGCGTCCCCATGCGCCGCC    JH1012 (c->deletion)
AGAAGTACCGAGTGAGCCTTCCCCTGGTTGACCCTGCAAAGTTCAGCAAGGGAGACGATG
CGATGTACACCTTGTCAGTCTGACAAGATTATGGGTGATCTTGTCAGACTGCACAAGTGT
ACCTCACATCGTCTGCCTTGCATGCGAGTGTAATGGGCGAGGAGTTCAGCAGACATTGTG
```

FIG. 6B

```
ATCTTCCTTGCACAACATGCATTCGATCTGTCAGACATCGCCTGCCGCACCTCGACCAAT
GTATGTGCTCTCTTTCATACCTTGGGTGTACCTCAGATGTCGGGTCCGTGAAAAAGTATA
ACCAGGTCCTGATGCCAGACGCACGTGTTGTGGCAGCTGCGCACACAGGCAGAGTTCGAG
GCGATGCAGAATGTGAAGGCGCCTGCCGGCAAACGCTACTTCCAGCACACCAAGCTGCCG
GACATCATCGGCGCGTACCCCTTCCGATCGGGGCTCACCGAGGCGCAGCAGGCGCATGAG
ACCGAGCGGCGCGAGGCCTTCCTCGATTTCCTCATGGGTGTCCTGGTGCGTACCTCTGCA
CCGGGGGATTCAGCATGCAATAAATGGGTGTTTGGTTCTGGCTGAGCACGAGATATTGAG
GCCGTGAAATGCACCACGGTCTGGAGAATATCACATGTTGGGGCTTCACACCTTCATCAT
TGTCTAAACAGGACCTGGACCCAGAGGTGCGCTGGAGCCCGCAGCAGGCGCTGCAGCATC
CATTCCTCACAGGGGCGCGTTTCACGGGCCATTCCAGCCGCCACCGCGCGTGCATGTGC
GCGCTCGGCCGGCCGCCGCGCCGCGCTCGGCCCCCGACGGCTCGGGCGTGATGTCGCCCT
ACAACTCCGCACTGTACAACTCCCCCGTGGCCACCATGCTGGCCACATCCCCCGAGTTCC
ATGCGCAGGCGCATGCTGCAGCAATGGCTGCTGTGCAGGCACGCGCCCTTCTTGATATTG
CCAAGGTGTCATGCGCAGAAATGTGTGTTGAATATTATGCATGATGGCACCTGGTTGGTT
GCCACCATGGAGGACAAAGTCGACGTTGAAACCGGACAAAGTGGCAAGTCATTGGCACTT
TCGTTGTTTCAATGTAGACTTTGTCCTCGTTGTCTGTGGCTGTGCAGACCCACGTTGTTT
TAGCATCCTTTAAAGAGAGCTTCTGGAGGCTCCACGGTCTTGGCTCAGTCCTGCAACAGA
TTGTGACTTTGCCATGCAGCATGTTTCAAATGCCTACAGAAATTGCATTGATTTTGATAC
AAACAAATCAGCTTTTAGTGCTTCCTGACGTGCTTGATGGCATTCTACAGGCGCATTTCA
GCCCGCGGGGAGCGGGCGCTCTTGGGGCCAGCTTGGGCGCTCCACAGCAGCAGAATTCCT
TCGAGCCGGCCATCGCGGTGGCTTCCGCCCTGGCCGCCGCACAGTACAACGGCATCCAGC
AGCAGGTGCCTGGCCTCGTTTTACCCCCCTGTATTAGAATTGCAAAAACTGCCTGGTTAG
ATAATCACTCCTTTTCAATGGCAGTATCGAGTGGGTGATGACGGGGCTGCTGGTGGCAGA
ATGGCATGCAGCAGCACACGCCGGCCGATCGTGCGCAGCAGGCGCAATATCAGCACAGCG
GGGCTGTGCACATACAGCAGCAGGCGCTGCATGGGATGCAGTATGGCTCCTTTGACCCTA
TGTATGCCAGCGGACACCACAGCTCGAGCCAGGTGGGGCTGCTTCCAAGCCTCTCTTAGA
TATGGTACTCAACTGCAGCTGCATTTTCGAGAAGCTGCTCATTCATGTGCTTTCTCTCGA
GCGCTCTTGCATGGGCTTGTTGTTCTCTTGCAGTGAGCTTCTCGAGATGAAATGTTTTTG
CTGGCATTCCTGGTAATGAGGGCTGTCGGGAAAAAACAAATTAAATTTGTCGAGATTGGG
GTCAGCCTAAAGTATCATATTTTCTAGGGGTCAGAGGGTTTCACTTACTATCTTGGCTTC
AATAACAATTCTCTTCTCTCGTCTTACGCGTGGTTTGATTGCTTGATGTCTTGCAGCAGA
CAGACACCCCATATGGAACGCCCTACGGGTCCTTCAGTGGGGGTTCCTTCAGCTCACTGA
GCAGCATGCAGACGCCGCCGCACTCGCTCAGCGGCTACTCGCCCATGACCCACCTCCATG
GCCTGCCCAGCTCCTATCACAGCACACCCGGCCGCTCTGGCGCCCATGCTGGCTCACTGC
AGGTGCTGTTCTAGCTATTGCAGTAAAAAATGGGTGTTTTGGTGGAAGGATGCACTCTTT
TGTGATCTTCGTGTTGTGGGAGGGAAATACGCCCTGGCCAGCTATCCTGTTTTTTTTAAC
AGATGAGATTGCAGGTCCCAGACCTTGGCGTGTCATATTACTGTGTTTCAAGAGGCATGA
TTGTCTGATCAACAGCACCTTCTCATTCAGCAGGACCACCGCAAGCAAGAAGAGCAGCTT
CATACAACATGCCTGTTCTGAACACTCTGGAAATGTACAGGGCACGCCCATGGCGACCTC
TTACAACAGCTACTCGTATCTGGCGGCGGCTGCCGCGGCGGCCTCGGCGCAGCAGGCGGC
ACAGCAGCCGGTGGTGGGCTCTCTGGAGACGCTGCGCGCAAACGCCATGTGGAATCTGCC
```

FIG. 6C

```
CCATGGCCCCGCCTTCCTGAATGGACAGCCCAACGCCGCCTACCTGGGCACCTCCCATGC
CCGGTGCGTTCTCAGTCAACTCAGAAAGTTTCTCTTTCATATACTTGCTCCTTCTGCGCA
CCCATGGATGATGATTACTGCAAGGCTACCATCACTGACTTTGCTATGCAGTGTTGGTGC
CAATTGGTCCCCACGAGAGCTGATAACGGCCCCTGAACAGCAAGGTCCCCAGGGGCATAA
ACCATATTGGAGTTGGTGAAAGTGCCTAAGGGCCTACTGATGGGCCTCATAATCACAAAG
CTCATTGGGGTGCCTGCTCGTGAGCAGGATCGGCAGCGGTGCATTCGGCGACGGCATGTT
GGGTAGCCTGCCCAGGGAGAACCTCCTGGGCACCCTCCAAGACGCAGACCACCACGGGGC
GCAGCAAGCAGCAGACAAACGCGCCAATTCAGGCCCATGCGCCAGCTCAGCGGAGATGGC
AGCGTGCTCACTGGGCAACTATGCAGGAAACGTGCTCCCAGACGGGCCGGCACAGCAGCA
GCAGCGCTTGGACCCCCAGCAGCAGTCCTGGCACTCCTTTACACAGTCCCTGCAGCAGTG
CACCTCGCCGCAGCAGGACAGGCATAGCAATACTGCAGGAATCGAGCTCCCACCTGGCGC
GTCTAACGGAGTATCCAGCGCACAGCAAGGCAGTGCAGCGGAGCAGCAGCAGCGGGGGGC
CCATCGGCCAGAACAGGCAACAGAGAGACAACAGCCAGATCAGGCACGGCTGCCCCCGGA
GCACCTGCCGCCGAAAGAGGCCACCAGCAGAAGGGTGCTCACCTATGAGGAGCACCTCCG
AGAGGAGGAGCTCAAGGCGCAGCTGGCCGAGCGCACTGGTGGGTCGTCTGCCGAGATAAC
ACATCCTGGCCCCCCTATTGCACAGCTGCTCACGCTCATAACGGGGACATGTCCGCCATC
TGCCAGCATACTCGTGTCAGGATGCATGCTGACTGGTGTAACATGCCACCTCCGGCCCGT
CCCGAGTGAGAAGCACTTCGATTCTGCAATGGGTACCACTGGGTCTCAGGTGTACCATAA
CCGTGGTTTTAAAATGTTACAAAGAAGAAGAAGAAGATTACCCATCATTCCAGCCGCCCA
TCATTCCAGCTGCCTAGGGTTGATCAGATGACCCACAACCACCCGCAGAATTCTTCAACA
CAGCAAAACAAGCCTGTATGAAACGAGCAACCTCAACAATGTCCTCCTGCCACATGAAAG
CCTGCATAGTTAAGGGTGACGTCTGACTGCACGTGCTAATGCGTCAGGTGGTGAAGCTGC
AGAGGGCACTGGGCGGGGGCGCCGGCTGCAAGCGCAGGCAACGGGGCGGCATCCTTGTC
GGAGGGCCGCACAAACATGTCGCGCACGCACTCACAGGATGTTGGCCCCACACCCAGCGA
CTGGGACCCCAGCTACAGGTCTGGCGCCCACCTTGCCCCCTGATCACGTTTCTGTCCTGC
TTGTTGAGCTTCCTCGTGGGATGCTCTCGTGGCCCTGCTCTGATCTGGGCAGTCCTTCCT
ACTGGATGGTGCTGTTCCTCCTGGATGTCAAGATGCGAAGATAGATTCATCTGAAAGGAT
TTGTCAGGACTGTATTTGTCTGGCCACCCTCATTACAGCGGGTCGCCATGGCCAGCACTG
GTTCTTGCTGCCTGCTGCAGCAAATGGCTGCCAGCAAACGATCGCTCGCTGGACAGTGCA
CCTTCATGCAGTTCTCCTGCCGATCCATTTTGCGGTACCGCAAAATGGATCGGCATCAAG
AAAGCAGGAGAATTGTACAAAGCTGCGCTCATCCAGCTGGCATTTGGCTGGCAGCCATTT
GCTGCAGCACAGCCAACTGATTGGCATCAATGGTGTCCAGTCTTGCATGCCCCATTAACT
TGTGGTGTACCAGCTTCTCACATGTCATTTGCATTATAATAGTAATGCTAGCTACCGTGA
TTGCTCGCTGATCCTAGCGCTGTGCTGTGTACATGTGCAGTGATGACCAGCTCCTCGATG
ATGCGGGATGGGCCAGGTTCCCCGACGGCCGCGCTCGGCAAAGCGCGCGAAGCGCGCTGC
TGCCGCGCTTTGCCGACACGGCCGCCGCCGCGGCCACCGATGCGGCGGGGGGCCCGCGC
AGCCGCAGCTTCCCGGCAGCTATGCGGAGTCACTCACGTCGCCGGTGCAGCCATCGCCGC
AGGGCCCCTACGACACGCACTGGCTGCGCTGCAATGGGGATGCCGCTCTCCGGCACGCCG
CCGCAGACACGCCCCTCTCGGTGCGCCTAACCTGGCTCTCCGCTGCATCTTTCTGGGCAG
AGTGTCTACTCTGACTGCGTTCCTTCTTTCTCCGTTTCTCTCCTACTTCTGTTTCTTTGT
AATCTTTCTTCGTAGTGTTCGTTGTGATGCAGTCACTGCTTTGTTTGTTTGCTTCTTCAT
```

FIG. 6D

```
GCTGTTCATGTTGGTGGTTGACATGTCACTGCTTGAAGGAGTGGTGCCGTGTATGTGCTT
TCAGCCATGGAATGTGTTTGTACAAATGCTGAGAATAGCTCATGAATGACACAGGCATTC
TAAGGTGTGTTTCTGTCTGGGGCTGCAGATGCTACCGGGCTCGTTGATACCCAAAGCGCC
CTACACAAGCATCGGTTTCGCCCCCGGCAAGAGATCTGGCTGCAATTGAGGTTGACCTGA
GCAGATGTCAACAGCCGCATTGCGGCAAGGGGCATCTGCTTCTGATCTCTGGGGCGCTCA
TTTTGGGGGCAGTCGAGGACAATGCTGTTGTGGCAGGCACCAACAAAGGTGCATTGAAGA
GGTTCTTCACCCATGGATCAAGGCATGCCACATGGTCTTTTGCCTGCACACTAGGATCAC
AGTCTGATGGCTGTGGATCCCTTACTGCTGCTGCTGCCCATATCTCAATTGGGTGGAAGG
CAAGCGGTGGCAGGCTCGAGTGTAAAGAGAGGGAGAGAGGGAGAGAGCTCGCTGCTTGAT
GTGGTCGCAGCTGTGGCTTGGGGCTTGCACTTATTCGTGTTGCAAATTCCTATCACATGT
CAGGGCATGGACATACTGGCATTGATCAGTGATGAGGTGCACTGCCAAAGGTGCCACTGG
CAGTGGAGCGTCGGCTCTGGACCAAGGTTTGGCACCAATTTTTACTCTTCATGGTGTGTA
GTGAGGTAGACTCTGTCTCTGCGGGTGCATGTATGTTTCAGTCTGTTTGTGAGCGCGAGT
GGCCTTGTGAGTAGTGAGCATTATTACTTGATCTGTGAGGTTTGGGCCCAGAGTAGCAGT
TCTTTGGCCATATTGGAGGTCATGACTGCAGTAGATAGATGGACCTGTGAACCTTCCTTG
TTGTTCCTAGCTAACCGCGCTGCATTGCATGCTGCCTGCATTTTATGTAGTCTCAGTCAA
CGTAGATATATCATTTGGGGCTTTAAGTCACAAGCGGGCAGCACCAGAGGTCCTGGCTTG
TTGACCTTGCTGTGAAGTACCGAAAACTTCCAAAAGCCCTGGATTTCTCCCCTGGCTGAT
GATAGAATCACACAGCCTCATGAGTGATCACTGCAACATGCCGGTTGGAATACAGTGAAA
GCATTTTTCGGTGCCAATGTAACGAGTGTTGGAAGTTGAAATGTGATCACAGTGCACTCA
TCAGAGCACCATTGACCTGCGCCCAGACAGCCTTGTAAGCTCTTGGCATGAGTGGCTTCA
GTCCTAGGAGGCCTGAAATCTTAAATGCCTATGGTATCACCGGTGGCATGTACATGTGAC
AACTATTCACCGTGAGTCACTGTGCATAATACCATCACTGATCACACGACCTGCATCACG
CAACAGCCATGCTCTTTACACTGCAGTGGCTGCGCAGCTGCAAATATATATCAGCAGTAA
TCATCATTGTCAAAGGTTTGCTGTCTTTTAATGAGCATGAATTAACAATGACAGCATAGG
TCTCTCCAGAAAGAAAGCACTTGATGCAGAAGGTTGCAACCTGAAACCTCATCAGTCAGC
TGCATACATTGTGACTGTACACATCCAACGGAAACATGCACACACCACCCCAGCAATTCC
AAGAGAAAGTTCCTTTGGGATAATAAATCACTGCCCGATAAAGCTTTGTCACACGCACAG
TGCAATTGACAGTCATACTGTATGTAGCAAAGCGCAACTTTAGCCCGGTGTATTTTGTTG
CGGACTTCTCTACACTGTACAAACCCTTGACAACTCAACCTAAGGCACAATGCTACACTG
GTGATGCACATGCAAAGCTTAAACAGCATCAGAGTCAGCTCAGCCAGGTCACAC
```

GREEN ALGA LIPID-ACCUMULATING VARIANT AND USE OF THE SAME

CROSS-REFERENCE TO RELATED APPLICATIONS

This application is a U.S. National Phase Application under 35 U.S.C. 371 of International Application No. PCT/JP2014/005594 filed on Nov. 7, 2014 and published in Japanese as WO 2015/075881 A1 on May 28, 2015. This application is based on and claims the benefit of priority from Japanese Patent Application No. 2013-239167 filed on Nov. 19, 2013. The entire disclosures of all of the above applications are incorporated herein by reference.

TECHNICAL FIELD

The present disclosure relates to a variant of a green alga with improved lipid productivity and a use thereof.

The present application is a patent application based on the results of research entrusted by the nation or the like (a patent application pursuant to Article 19 of the Industrial Technology Enhancement Act with respect to the entrusted research projects: 2013, Ministry of Agriculture, Forestry and Fisheries, a project for the production and the use of renewable energy using local resources, an entrusted project for developing a technique for manufacturing an alternative fuel to petroleum or the like using a microalga; and 2013, New Energy and Industrial Technology Development Organization, biomass energy technology development, a strategic project for developing a utilization technique of next-generation biomass energy, "Research and Development of Breeding and Modification Techniques of a Microalga with Excellent Oil Productivity").

BACKGROUND ART

Production of an industrial product such as a biodiesel fuel and a food product (hereinafter, referred to as "a biofuel or the like") from a fatty acid produced by a unicellular photosynthetic organism (hereinafter, referred to as a "microalga") or from a compound (hereinafter, referred to as a "lipid") which releases a fatty acid by hydrolysis has been studied intensively all over the world. The inventors of the present application have found the following with respect to the lipid production.

At present, the production of a biofuel or the like on a commercial basis may be difficult due to high production cost. Thus, development of a technique reducing the production cost of a biofuel or the like may be necessary (for example, Non-Patent Literature 1).

In an attempt to isolate a microalga with increased lipid productivity and thus to contribute to the cost reduction, some studies have already been conducted. In general, a photosynthetic organism has excessive antenna chlorophyll, which reduces the efficiency for light utilization. Therefore, it has been confirmed that the biomass productivity is improved by reducing the antenna chlorophyll content (Non-Patent Literatures 2 to 4).

In addition, with the intention of reducing labor for lipid recovery, strains which secrete lipids into extracellular spaces have been produced. However, the strains have not been put to practical use (Non-Patent Literatures 5 and 6).

Compared to the enormous interest in the biofuel production using a microalga and compared to the high number of reviews of biofuel processes using microalgal biomass and breeding of microalgae, a very small number of strains have been developed, as described above.

Strain *Pseudochoricystis ellipsoidea* (*P. ellipsoidea*) has been reported by Satoh et al. (Non-Patent Literature 7). The genus and species names of this strain are not according to the International Code of Nomenclature for algae, fungi, and plants but are tentative names. The subsequent phylogenetic analysis using genes has demonstrated that the strain is a close relative of *Coccomyxa* and *Pseudococcomyxa*. The strain, like other microalgae, accumulates lipids in the cell when the nitrogen source in the culture medium is depleted (Non-Patent Literature 8). The mechanism of the lipid accumulation induced by the depletion of the nitrogen source has not been revealed yet, but it is speculated that lipids are accumulated as a result of the cell response to the stress of nitrogen depletion (Non-Patent Literature 9).

The inventors of the present application have been working on breeding *P. ellipsoidea* and improving large-scale cultivation techniques. For example, as described in Patent Literature 1, the inventors have succeeded in culturing two *P. ellipsoidea* strains (strain Obi and strain N1: Patent Literature 2) in an outdoor open system for a long time.

Similar to general photosynthetic organisms, *P. ellipsoidea* also has excessive antenna chlorophyll, which reduces the efficiency for light utilization. Patent Literature 3 discloses that strain 5P with a reduced antenna chlorophyll content was isolated using *P. ellipsoidea* strain Obi as the parental strain. The biomass productivity of strain 5P was superior to that of the wild-type strain (Patent Literature 3).

*P. ellipsoidea* is a strain suitable for outdoor cultivation on a large scale and may be considered as one of the most promising strains as the raw materials for the commercial lipid production. Further improvement of the lipid productivity and the reduction in the lipid production cost are desired.

PRIOR ART LITERATURES

Patent Literatures

Patent Literature 1: JP 2013-90598 A
Patent Literature 2: JP 2013-102748 A
Patent Literature 3: JP 2013-102715 A

Non-Patent Literatures

Non-Patent Literature 1: Chisti Y. (2013) Constraints to commercialization of algal fuels. J. Biotechnol. 167:201-214.
Non-Patent Literature 2: Nakajima Y, Ueda R. (1997) Improvement of photosynthesis in dense microalgal suspensions by reduction of light harvesting pigments. J. Appl. Phycol. 9:503-510.
Non-Patent Literature 3: Nakajima Y, Ueda R. (2000) The effect of reducing light-harvesting pigments on marine microalgal productivity. J. Appl. Phycol. 12:285-290.
Non-Patent Literature 4: Oey M, Ross I L, Stephens E, Steinbeck J, Wolf J, Radzun K F, Kugler J, Ringsmuth A K, Kruse O, Hankamer B. (2013) RNAi knock-down of LHCBM1, 2 and 3 increases photosynthetic H2 production efficiency of the green alga *Chlamydomonas reinhardtii*. PLOS One 8, e61735.
Non-Patent Literature 5: Liu X, Curtiss III F R. (2009) Nickel-inducible lysis system in *Synechocystis* sp. PCC6803. Proc. Natl. Acad. Sci. USA. 106:21550-21554.

Non-Patent Literature 6: Liu X, Sheng J, Curtiss III R. (2011) Fatty acid production in genetically modified cyanobacteria. Proc. Natl. Acad. Sci. USA. 108:6899-6904.

Non-Patent Literature 7: Satoh A, Kato M, Yamato T, Ikegami Y, Sekiguchi H, Kurano, N, Miyachi S. (2010) Characterization of the lipid accumulation in a new microalgal species, *Pseudochoricystis ellipsoidea* (Trebouxiophyceae). J. Jap. Inst. Energy 89, 909-913 (September 2010)

Non-Patent Literature 8: Ito T, Tanaka M, Shinkawa H, Nakada T, Ano Y, Kurano N, Soga T, Tomita M. (2013) Metabolic and morphological changes of an oil accumulating trebouxiophycean alga in nitrogen-deficient conditions. Metabolomics. 9:178-187.

Non-Patent Literature 9: Wang Z T, Ullrich N, Joo S, Waffenschmidt S, Goodenough U. (2009) Algal lipid bodies: stress induction, purification, and biochemical characterization in wild-type and starchless *Chlamydomonas reinhardtii*. Eukaryot Cell. 8:1856-1868.

SUMMARY OF INVENTION

It is an object of the present disclosure to provide a lipid production method using a green alga with isolation of a green alga with improved lipid productivity.

According to one example of the present disclosure, a green alga variant, which has a dual-specificity tyrosine-phosphorylation regulated protein kinase (DYRK) activity that is reduced compared to a dual-specificity tyrosine-phosphorylation regulated protein kinase (DYRK) activity of a parental strain, is provided. A lipid production of a green alga variant per unit time and per unit culture area is increased compared to the lipid production of the parental strain. A dual-specificity tyrosine-phosphorylation regulated protein kinase of the parental strain is a protein having an amino acid sequence with at least 50% sequence identity with the amino acid sequence of an active site and a substrate recognition site of SEQ ID NO: 4, and having the dual-specificity tyrosine-phosphorylation regulated protein kinase activity.

According to an example of the present disclosure, it may be possible to produce a green alga with improved lipid productivity. By culturing the variant of the green alga according to the present disclosure, it may be possible to considerably reduce the production cost of a lipid used for a biofuel or the like.

Furthermore, according to an example of the present disclosure, a method for producing a lipid by isolating a green alga with improved lipid productivity to use the green alga is provided.

BRIEF DESCRIPTION OF DRAWINGS

The above and other aspects, features and advantages of the present disclosure will become more apparent from the following detailed description made with reference to the accompanying drawings. In the drawings:

FIG. 6A is a diagram illustrating mutations in LMR-DYRK gene of the variants of *P. ellipsoidea* including strains JH1011, JH1012 and JH1013 have;

FIG. 6B is a diagram continuing from FIG. 6A;

FIG. 6C is a diagram continuing from FIG. 6B; and

FIG. 6D is a diagram continuing from FIG. 6C.

DESCRIPTION OF EMBODIMENTS

Figures 1, 2, 3A:
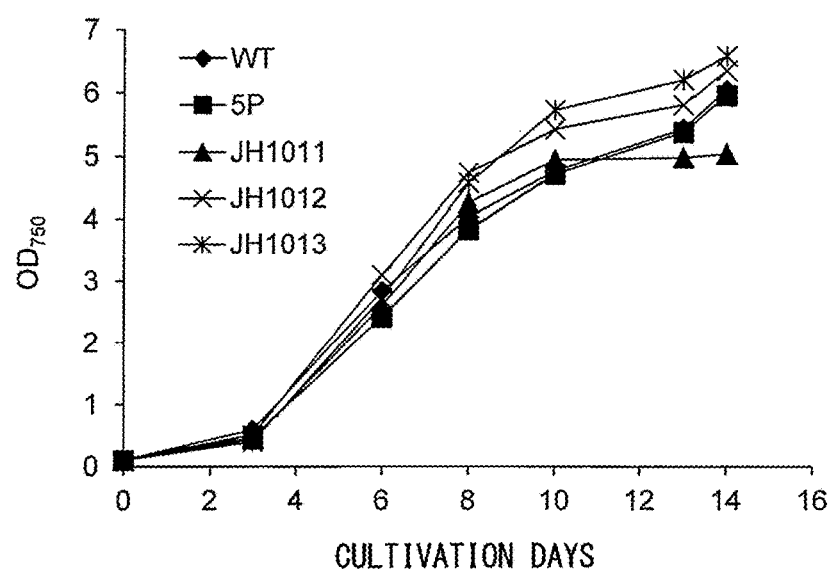
FIG. 1 is a diagram showing an active site and a substrate recognition site of a DYRK.
FIG. 2 is a diagram showing examples of primers used for amplifying a partial nucleotide sequence of a DYRK subfamily gene by PCR.
FIG. 3A is a diagram illustrating a graph of the growth of *P. ellipsoidea* strain Obi (WT) and Obi-derived variants including strains 5P, JH1011, JH1012 and JH1013.

The present disclosure relates, for example, to a variant of a green alga which has a reduced dual-specificity tyrosine-phosphorylation regulated protein kinase (DYRK: Dual-specificity tYrosine-phosphorylation Regulated protein Kinase) activity and which thus has improved lipid productivity compared to that of the parental strain or the wild-type strain and relates to a use thereof.

The present disclosure relates to a variant of a green alga in which the lipid production per unit time and per unit culture area is improved compared to that of the parental strain (or the wild-type strain) and which has a reduced DYRK activity.

One of the most important issues for reducing the cost of production of a biofuel or the like from a microalga-derived lipid is considerable improvement of the lipid productivity of the microalga. The inventors of the present application have found that the lipid productivity of a green alga can be improved considerably by causing a defect in the protein (the genomic DNA sequence of SEQ ID NO:1, the mRNA sequence of SEQ ID NO:2) of the DYRK subfamily which has the amino acid sequence of SEQ ID NO:3 and which is derived from *Pseudochoricystis ellipsoidea* (*P. ellipsoidea*) (tentative name) strain Obi (accession number FERM BP-10484; Japanese Patent No. 4748154 (called *Pseudochoricystis ellipsoidea* Sekiguchi et Kurano gen. et sp. nov. strain MBIC11204 in the patent)) belonging to Viridiplantae, Chlorophyta (hereinafter, referred to as a "green alga"). The inventors thus have completed the present disclosure.

Strain MBIC11204 was deposited at National Institute of Advanced Industrial Science and Technology, International Patent Organism Depositary (IPOD; current NITE-IPOD) (Central 6, 1-1-1 Higashi, Tsukuba, Ibaraki) on Feb. 15, 2005 and was given an accession number FERM P-20401. Strain MBIC11204 was transferred to an international depositary authority under the Budapest Treaty on Jan. 18, 2006 and was given an accession number FERM BP-10484.

DYRK belongs to the CMGC serine/threonine protein kinase family and is a protein kinase which is found in many eukaryotes and which is involved in the regulation of transduction of various signals. The findings of the inventors of the present application suggested that the DYRK of *P. ellipsoidea* negatively regulates the lipid production. Thus, a DYRK which negatively regulates the lipid production is called a Lipid-Metabolism-Regulating DYRK (abbreviated to "LMR-DYRK") hereinafter, and distinguished from other DYRKs. According to the findings, the lipid productivity of a green alga can be improved by reducing the LMR-DYRK activity through genetic manipulation, and the production cost of a lipid used for a biofuel or the like can be reduced considerably by culturing a strain with a reduced LMR-DYRK activity.

The response of plants to various types of environmental stress has been studied using *Arabidopsis* or the like. It has been revealed that many protein kinases are involved in the response to environmental stress (Wang P, Xue L, Batelli G, Lee S, Hou Y J, Van Oosten M J, Zhang H, Tao W A, Zhu J K. (2013) Quantitative phosphorproteomics identifies SnRK2 protein kinase substrates and reveals the effectors of abscisic acid action. Proc Natl Acad Sci USA. 110:11205-11210). According to the present disclosure, it was revealed that an LMR-DYRK belonging to the CMGC serine/threonine protein kinase family partially inhibits the fat-accumulation reaction caused in response to the stress of nitrogen depletion.

In the present disclosure, examples of the lipid produced by a green alga include neutral fat such as triglycerides, sterol esters and hydrocarbons, glycolipids such as galactosyl diglycerides, and phospholipids such as phosphatidylglycerol.

Examples of the green alga include green algae belonging to Trebouxiophyceae. Examples of green algae belonging to Trebouxiophyceae include green algae belonging to *Trebouxia*, *Chlorella*, *Botryococcus*, *Choricystis*, *Coccomyxa* and *Pseudococcomyxa*. Specific species belonging to *Coccomyxa* and *Pseudococcomyxa* include *Coccomyxa subellipsoidea* (Blanc G, Agarkova I, Grimwood J, Kuo A, Brueggeman A, Dunigan D D, Gurnon J, Ladunga I, Lindquist E, Lucas S, Pangilinan J, Proschold T, Salamov A, Schmutz J, Weeks D, Yamada T, Lomsadze A, Borodovsky M, Claverie J M, Grigoriev I V, Van Etten J L. (2012) The genome of the polar eukaryotic microalga *Coccomyxa subellipsoidea* reveals traits of cold adaptation. Genome Biol. 13:R39 (PMID: 22630137)) and *Pseudococcomyxa simplex* (Broady P A. (1987) The morphology, distribution and ecology of *Pseudococcomyxa simplex* (Mainx) Fott (Chlorophyta, Chlorellaceae), a widespread terrestrial antarctic alga. Polar Biol 7:25-30). Specific strains belonging to Trebouxiophyceae include *P. ellipsoidea* strain Obi (accession number FERM BP-10484; Japanese Patent No. 4748154) and a variant strain thereof, *P. ellipsoidea* strain 5P (accession number FERM P-22179; Patent Literature 3). In this regard, *P. ellipsoidea* strain Obi and *P. ellipsoidea* strain 5P have the same gene encoding an LMR-DYRK (the genomic DNA sequence of SEQ ID NO:1, the mRNA sequence of SEQ ID NO:2, the amino acid sequence of SEQ ID NO:3).

As described in Patent Literature 3, the strain of FERM P-22179 was deposited at National Institute of Advanced Industrial Science and Technology, International Patent Organism Depositary (IPOD) (Central 6, 1-1-1 Higashi, Tsukuba, Ibaraki) on Oct. 21, 2011 and was given an accession number FERM AP-22179.

Examples of green algae other than the green algae belonging to Trebouxiophyceae include green algae belonging to *Chlamydomonas* and *Scenedesmus*.

The variant of the green alga according to the present disclosure is a green alga obtained by subjecting one of the above green algae as a parental strain to a method for reducing the LMR-DYRK activity.

In the present disclosure, an example of the gene encoding an LMR-DYRK (hereinafter, referred to as "the LMR-DYRK gene") is a gene encoding a protein which has a DYRK activity and which has an amino acid sequence with at least 50% sequence identity, preferably at least 65% identity, particularly preferably at least 80% identity, most preferably at least 85% identity, at least 90% identity, at least 95% or 100% identity with the amino acid sequence of the active site and the substrate recognition site of the LMR-DYRK shown in FIG. 1 (the amino acid sequence of SEQ ID NO:4; corresponding to the 175th to 257th amino acid residues of SEQ ID NO:3). The active site and the substrate recognition site of the LMR-DYRK shown in FIG. 1 are the active site and the substrate recognition site of *P. ellipsoidea* DYRK which were predicted from the conformation of human DYRK (DYRK1A) (Soundararajan M, Roos A K, Savitsky P, Filippakopoulos P, Kettenbach A N, Olsen J V, Gerber S A, Eswaran J, Knapp S, Elkins J M. (2013) Structures of Down syndrome kinases, DYRKs, reveal mechanisms of kinase activation and substrate recognition. Structure 21:986-996). In FIG. 1, the sites which are suggested to be important for the activity and the substrate recognition are underlined.

Examples of the LMR-DYRK gene include: DNA which encodes a protein having a DYRK activity and which includes a nucleotide sequence with at least 50% sequence identity, preferably at least 58% identity, particularly preferably at least 65% identity, at least 80% identity, most preferably at least 85% identity, at least 90% identity, at least 95% or 100% identity with the genomic DNA including the nucleotide sequence of SEQ ID NO:1 derived from *P. ellipsoidea* strain Obi (the initiation codon: the 558th to 560th base sequences, the stop codon: the 7607th to 7609th base sequences) (the nucleotide sequence of SEQ ID NO:2 corresponds to its mRNA, and the 388th to 3495th base sequences of SEQ ID NO:2 are the coding region (CDS)); or DNA which includes a nucleotide sequence with one to several (for example one to ten, preferably one to five, more preferably one to three, further preferably one or two) base deletions, substitutions, additions or insertions compared to the nucleotide sequence of SEQ ID NO:1 and which encodes a protein having a DYRK activity.

Incidentally, one base deletion, substitution, addition or insertion here refers to one site. Several dozen bases may be deleted or inserted at the site.

Moreover, examples of the LMR-DYRK gene include: DNA encoding a protein which has a DYRK activity and which has an amino acid sequence with at least 50% sequence identity, preferably at least 65% identity, particularly preferably at least 80% identity, most preferably at least 85% identity, at least 90% identity, at least 95% or 100% identity with the amino acid sequence of SEQ ID NO:3 derived from *P. ellipsoidea* strain Obi; or DNA encoding a protein which has an amino acid sequence with one to several (for example one to ten, preferably one to five, more preferably one to three, further preferably one or two) amino acid deletions, substitutions, additions or insertions compared to the amino acid sequence of SEQ ID NO:3 and which has a DYRK activity.

The "DYRK activity" means the activity of autophosphorylating the tyrosine residues in the DYRK active site. The DYRK activity can be measured by various methods and can be measured by known methods, for example by detecting the autophosphorylated protein through western blotting using a commercial anti-phosphotyrosine antibody.

In the present disclosure, the variant of the green alga according to the present disclosure can be obtained by subjecting a parental green algal strain to a method reducing the activity of the DYRK encoded by the LMR-DYRK gene explained above.

Examples of the method to reduce the DYRK activity include:

(1) a method of disrupting the LMR-DYRK gene;
(2) a method of suppressing the transcription of the LMR-DYRK gene and reducing the expression of the gene; and
(3) a method of suppressing the translation of the LMR-DYRK gene and reducing the translation efficiency of the gene.

(1) Method of Disrupting LMR-DYRK Gene

In the present disclosure, the LMR-DYRK gene-disrupted green algal strain means a green algal strain in which at least one or more of the original LMR-DYRK genes, including an allele, an isomer or the like, have been disrupted.

In a method for disrupting the LMR-DYRK gene, a mutation causing a base substitution, deletion, insertion and/or addition is introduced to the DNA of the LMR-DYRK gene region or the upstream promoter region on the genomic DNA of a green alga.

(2) Method of Suppressing Transcription of LMR-DYRK Gene and Reducing Expression of Gene In a method of suppressing the transcription of the LMR-DYRK gene, a variant of a green alga is prepared by substituting the transcriptional promoter region of the LMR-DYRK gene of the target green alga with a promoter which represses the transcription, and the variant of the green alga is cultured under conditions repressing the transcription.

A variant produced by inserting a nucleotide sequence having a transcription-repressing activity into the region involved in the transcription of the LMR-DYRK gene of a green alga may also be used.

(3) Method of Suppressing Translation of LMR-DYRK Gene and Reducing Translation Efficiency of Gene An example of the method of suppressing the translation of the LMR-DYRK gene is a method using an antisense RNA (for example, the RNAi method). That is, a gene from which antisense RNA complementary to the mRNA of the LMR-DYRK gene is transcribed is incorporated into a green algal genome, and the antisense RNA is overexpressed. The translation of the mRNA of the LMR-DYRK gene is suppressed.

Specifically, the variant of the green alga with a reduced LMR-DYRK activity according to the present disclosure can be produced in accordance with the following procedures. That is, a mutagenic substance is acted on a parental green algal strain, and then a variant with increased lipid content is chosen by screening. It is confirmed that a mutation has been introduced in the LMR-DYRK gene of the obtained variant. In this manner, the variant of the green alga can be produced.

Alternatively, the variant of the green alga with a reduced LMR-DYRK activity according to the present disclosure can be produced more efficiently through the following two-stage gene manipulation.

(i) Determination of Partial Nucleotide Sequence of LMR-DYRK Gene

A partial nucleotide sequence of the LMR-DYRK gene of a target green alga whose lipid productivity is to be improved is determined by the following procedures. Proteins belonging to the DYRK subfamily, including the LMR-DYRK encoded by the gene having the nucleotide sequence of SEQ ID NO:1 derived from *P. ellipsoidea* strain Obi, share a highly conserved amino acid sequence. Thus, a DNA fragment is amplified by PCR amplification using PCR primers designed based on the conserved amino acid sequence and is cloned in *Escherichia coli*. Then, the nucleotide sequence of the DNA fragment is determined. Examples of the primers used for the PCR amplification are shown in FIG. 2. The forward primer (SEQ ID NO: 5) in FIG. 2 is designed based on the conserved amino acid sequence (IHCDLKPEN). On the other hand, the reverse primers (SEQ ID NOs: 6 and 7) are designed based on an amino acid sequence (IDMWSLGC). It is expected that one of the two reverse primers achieves the PCR amplification. The nucleotide sequence is determined according to the IUPAC standard.

Incidentally, the sequence of SEQ ID NO: 5 is, from the 5' end, ATCCACTGCG ACCTNAARCC NGARAA. The sequence of SEQ ID NO: 6 is, from the 5' end, CAGCCCA-RRC TCCACATRTC DAT. The sequence of SEQ ID NO: 7 is, from the 5' end, CAGCCCARNG ACCACATRTC DAT.

In some cases, an organism has multiple DYRK genes. Direct sequencing of the PCR-amplified DNA fragments should be avoided. When the partial DYRK gene sequence thus obtained is extended, the inverse PCR method (Huang S H. (1994) Inverse polymerase chain reaction. An efficient approach to cloning cDNA ends. Mol Biotechnol. 12:15-22) or the like may be used. Recently, next-generation sequencing methods have made progress, and determination of whole genome sequences has become very easy. Thus, the whole genome sequence of the target green alga may be determined first, and a sequence which is the closest to the *P. ellipsoidea* strain Obi-derived LMR-DYRK gene sequence of SEQ ID NO: 1 may be selected from the genome sequence as a candidate LMR-DYRK gene.

(ii) Knockout of Candidate LMR-DYRK Gene

When the nucleotide sequence of a candidate LMR-DYRK gene has been determined, a variant having a defect in the gene can be produced using the gene knockout method called ZFN, TALEN or CRISPR/Cas (Gaj T, Gersbach C A, Barbas C F 3rd. (2013) ZFN, TALEN, and CRISPR/Cas-based methods for genome engineering. Trends Biotechnol. 31:397-405).

(iii) Knockdown of Candidate LMR-DYRK Gene

Alternatively, the expression of the LMR-DYRK can be repressed using the RNAi method (Cerutti H, Ma X, Msanne J, Repas T. (2011) RNA-mediated silencing in Algae: biological roles and tools for analysis of gene function. Eukaryot Cell. 10:1164-1172).

The lipid productivity of the variant of the green alga thus obtained is measured by the method or the like described in Example 1. When the improvement of the lipid productivity is confirmed, the production of the variant of the green alga with a reduced LMR-DYRK activity according to the present disclosure is completed.

In the variant of the green alga according to the present disclosure, the lipid production per unit time and per unit culture area is significantly (for example, 1.1 times or more, preferably 1.3 times or more) higher than in the parental strain or the wild-type strain. The lipid production per unit time and per unit culture area can be represented by the lipid production (gram) per cultivation period (a day), per culture area ($m^2$) ($g/m^2/day$), for example.

The present disclosure includes a lipid production method including culturing (on a large scale) the variant of the green alga according to the present disclosure described above and producing a lipid. As the large-scale culture method, the culture method which has already been established and which is described in JP 2012-273633 A (title of invention: Culture Method and Culture System for Microalgae) or the like can be used. Specifically, the method is a method in which a microalga is cultured using a culture liquid having pH of 4 or less and including ammonia nitrogen. According to the culture method, other microalgae and protists do not proliferate easily because the pH of the solution is 4 or less, and in particular, the proliferation of other microalgae and protists is further prevented because the culture liquid includes ammonia nitrogen (such as urea). Due to these effects, it may be possible to easily achieve large-scale cultivation in the open air. Another feature is that the pH of the culture liquid does not change easily because bicarbonate ion is not generated even when $CO_2$ is introduced to the culture liquid. Furthermore, when the nitrogen source is urea, the pH values of the culture medium before and after the cultivation are the same. Thus, the whole or a part of the microalgal population can be recovered from the culture liquid used for the cultivation of the microalga, and a new microalga can be cultured using the culture liquid remained after the recovery. In this case, since the culture liquid can be reused, it may be possible to significantly reduce the cultivation cost of a microalga.

A lipid can be obtained after the cultivation from the culture by extraction using, for example, hexane or the like.

EXAMPLES

Hereinafter, the present disclosure is explained in further detail using Examples. The technical scope of the present disclosure should not be limited to these Examples.

(Example 1) Isolation of High Lipid-Accumulating Variants of *P. ellipsoidea*

1-1. Isolation of High Lipid-Accumulating Variants of *P. ellipsoidea*

*P. ellipsoidea* strain 5P (accession number FERM P-22179; Patent Literature 3) was cultured in MA5 medium (1.5 g of sodium nitrate, 100 mg of magnesium sulfate, 35 mg of potassium dihydrogen phosphate, 45 mg of dipotassium hydrogen phosphate, 9 mg of calcium chloride, 19.6 mg of ferric ammonium citrate, 12 mg of citric acid, 2 mg of EDTA-2Na, 0.07 mg of boric acid, 0.15 mg of manganese sulfate, 0.30 mg of zinc sulfate, 0.3 mg of copper sulfate, 0.003 mg of sodium molybdate, 0.07 mg of cobalt chloride and 4.76 g of HEPES in 1 L of distilled water (pH 7.0)) under a plant-fluorescent light with light intensity of 100 $\mu$mol m$^{-2}$ s$^{-1}$ while blowing air bubbles including 1% $CO_2$ (unless otherwise mentioned, liquid cultivation was conducted under the same culture conditions below).

Cells in the logarithmic growth phase were collected by centrifugation (3,000 rpm, 5 min), suspended in a citrate buffer solution (0.1 M, pH 5.5) and then treated with 500 µg/ml NTG (nitrosoguanidine (1-methyl-2-nitro-1-nitrosoguanidine)) for an hour at room temperature. After washing the treated cells with a phosphate buffer solution (0.1 M, pH 7.0), the cells were suspended in the MA5 medium and cultured.

After the cultivation, the lipids in the cells were fluorescently stained with 200 µM BODIPY 505/515, and cells with high fluorescence intensities, which were considered to have high lipid contents, were concentrated using a cell sorter (FACS). The cells concentrated were cultured in the MA5 medium. After the cultivation, the concentration with the cell sorter was conducted again. The cycle of "concentration by the cell sorter and cultivation" was repeated three times. Then, *P. ellipsoidea* cells in the last culture liquid were spread on MA5 agar culture, and the single colonies which grew were each seeded on a new plate.

The strains which were thus established from about 100 single colonies were each subjected to liquid cultivation. Through measurement of the fluorescence intensities and evaluation of the growth rates, variant strains which had growth rates equal to that of the wild-type strain and in which the BODIPY 505/515 fluorescence per cell increased compared to that of the wild-type were selected.

The candidate high lipid-accumulating variants thus obtained were cultured in A6 medium (50 mg of ammonium sulfate, 150 mg of urea, 100 mg of magnesium sulfate heptahydrate, 35 mg of potassium dihydrogen phosphate, 45 mg of dipotassium hydrogen phosphate, 9 mg of calcium chloride dihydrate, 19.6 mg of ferric ammonium citrate, 12 mg of citric acid, 2 mg of EDTA-2Na, 0.07 mg of boric acid, 0.15 mg of manganese sulfate, 0.30 mg of zinc sulfate, 0.3 mg of copper sulfate, 0.003 mg of sodium molybdate and 0.07 mg of cobalt chloride in 1 L of distilled water (pH 4.0)), and the dry weights and the lipid contents were measured over time.

The lipid content of *P. ellipsoidea* increases after the nitrogen source is depleted. Thus, the cells which were pre-cultured in the MA5 medium or the A6 medium were transferred to MA5 medium or A6 medium with no nitrogen source. Samples were taken 0, 3, 6, 9, 12, 15 and 18 days after the transfer, and the dry weights and the lipid contents were measured.

1-2. Measurement of Lipid Contents

The lipid contents were measured by two methods. In the first method, lipids were extracted, methyl-esterified and then quantified by GC-FID. After drying a cell culture liquid at 105° C., the dry culture was collected on a GF/F glass filter, which had been weighed, and washed with distilled water. Then, the dry weight was measured. Also, cells were collected from the same amount of the culture liquid by centrifugation, suspended in 0.1 N HCl and subjected to heat treatment at 100° C. for five minutes, and the lipids were extracted by the Bligh-Dyer method (Bligh E G and Dyer W J. (1959) A rapid method for total lipid extraction and purification. Can J Biochem Physiol. 37:911-917). A certain amount of n-pentadecane was added to the lipids as an internal control.

The extracted sample was dried and solidified using a centrifugal concentration apparatus, and fatty acid methyl esters were collected using a fatty acid methylation kit (manufactured by Nacalai Tesque, Inc.) and a methyl ester purification kit (manufactured by Nacalai Tesque, Inc.) and then dried and solidified again. The dry sample was dissolved in 5 ml of n-hexane to obtain a fatty acid methyl ester sample, and the sample was quantified by GC-FID under the following conditions.

Apparatus: Shimadzu GC-2010 Plus
Column: factor FOUR VF-5 ms, 0.20 nm (inside diameter), 30 m (length), 0.33 µm (thickness)
Temperature: 100° C. (2 min)-20° C./min-310° C. (10 min)
Vaporizing chamber: 240° C. Splitless
Detector: FID 320° C.
Carrier Gas: He The components quantified were methyl ester compounds of C16:0, C16:1, C18:0, C18:1, C18:2, C20:0 and C20:1, which were the main components. The amount of the triglycerides accumulated in the cells was estimated from the concentrations.

In addition, as the second method, the oil content was also measured by NMR. Cells were harvested by centrifugation at 8,000 rpm for five minutes or longer and freeze-dried. Then, about 40 mg of the cells was taken and weighed, and the oil content per unit dry weight was measured using the MQC-type oil content analyzer manufactured by Oxford Instruments. The calibration curve was drawn using olive oil according to the Japanese Pharmacopoeia as the standard substance.

The lipid productivity (mg $d^{-1}$ $L^{-1}$) in 1 L of culture medium was defined as the value derived by multiplying the lipid content (%) per dry weight and the dry weight (mg $L^{-1}$) of 1 L of the culture liquid and dividing the resultant by the cultivation days.

From the above experiment, three strains with excellent lipid productivity in 1 L of culture medium were selected and named JH1011, JH1012 and JH1013.

Figure 3B:
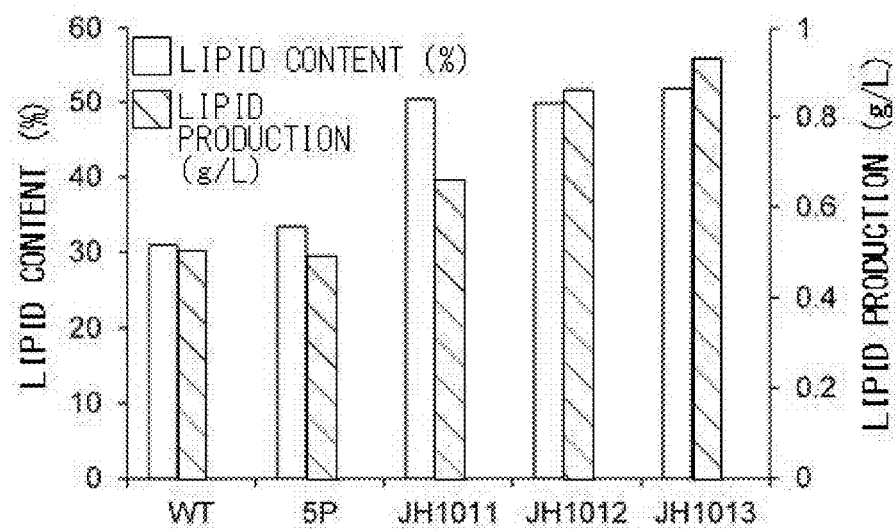
FIG. 3B is a diagram illustrating a graph of the lipid production of *P. ellipsoidea* strain Obi (WT) and the Obi-derived variants including strains 5P, JH1011, JH1012 and JH1013.

The changes in the intracellular lipid contents of strains JH1011, JH1012 and JH1013 are shown in FIG. 3A and FIG. 3B. It can be recognized that, in strains JH1011, JH1012 and JH1013, the lipid contents increased remarkably compared to those of the wild-type strain, strain Obi (WT), and strain 5P, which is the direct parental strain of these variant strains (strains JH1011, JH1012 and JH1013). In other words, while the maximum lipid contents of the wild-type and strain 5P were around 30%, the maximum lipid contents of strains JH1011, JH1012 and JH1013 exceeded 50% (FIG. 3B). The strains were cultured using the A6 medium, and the lipid productivity was evaluated after 14 days.

The lipid productivity in 1 L of culture medium of each of strains JH1011, JH1012 and JH1013 is also shown in FIG. 3B. It can be seen that, in strains JH1011, JH1012 and JH1013, the lipid productivity in 1 L of culture medium increased remarkably compared to those of the wild-type strain, strain Obi (WT), and strain 5P, which is the direct parental strain of these variants.

1-3. Evaluation of Cultivation Using Raceway

Figure 4:
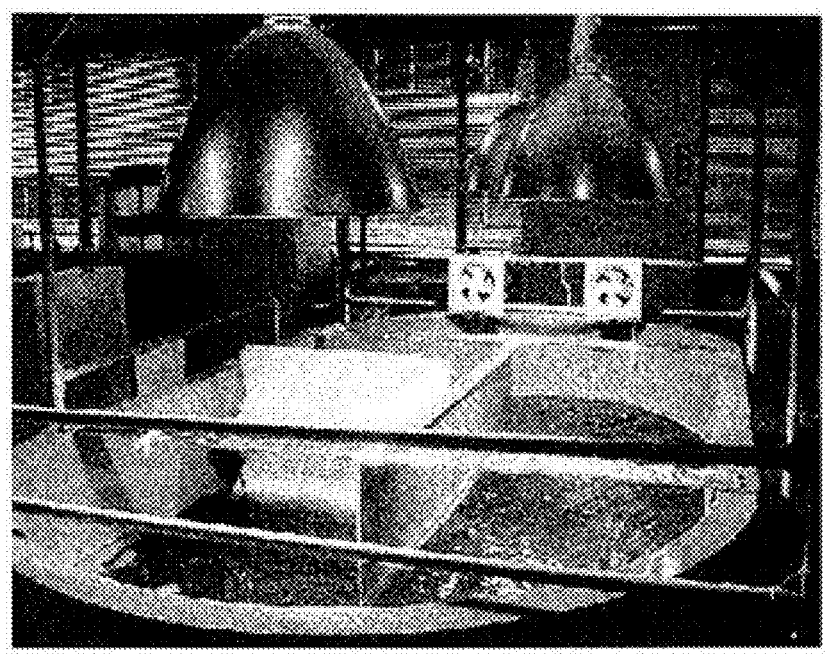
FIG. 4 is a diagram illustrating an appearance of a raceway culture system.

Using a raceway system installed indoors (FIG. 4), a test for evaluating the lipid productivity of strains JH1011, JH1012 and JH1013 was conducted. The installation area of the raceway was 3.8 $m^2$, and the set volume was 490 L. The cultivation was conducted under the conditions of a radiation intensity of 200-300 µmol $m^{-2}$ $sec^{-1}$, a light-dark cycle of 12 h/12 h and a $CO_2$ concentration of 1%. The composition of the culture medium used was as follows: 45 mg of ammonium sulfate, 30 mg of magnesium sulfate heptahydrate, 10 mg of potassium dihydrogen phosphate, 5 mg of dipotassium hydrogen phosphate, 10 mg of calcium chloride dihydrate, 10 mg of calcium carbonate, 2 mg of ferric citrate, 2 mg of citric acid, 2 mg of EDTA-2Na, 0.07 mg of boric acid, 0.15 mg of manganese sulfate, 0.30 mg of zinc sulfate, 0.3 mg of copper sulfate, 0.003 mg of sodium molybdate, 0.07 mg of cobalt chloride, 2 µg of biotin, 10 µg of thiamine HCl, 1 µg of vitamin B6, 1 µg of vitamin B12 in 1 L of distilled water (pH 4.0).

The dry weights of the algae in 1 L of the culture medium were measured during the cultivation period. After the completion of the cultivation, the recovered algae were freeze-dried, and the oil contents were measured using the MQC-type oil content analyzer manufactured by Oxford Instruments as described in the section 1-2.

Figure 5A:
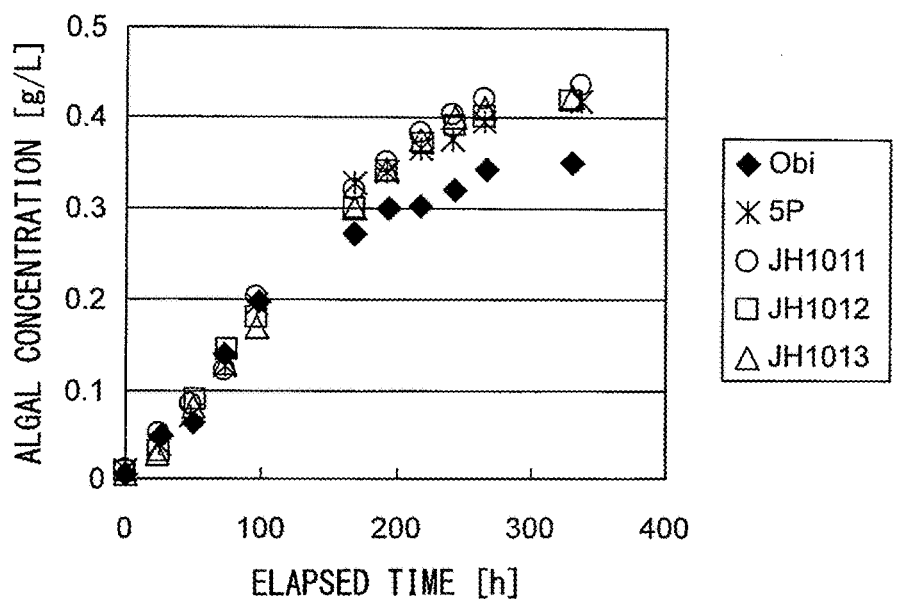
FIG. 5A is a diagram illustrating a graph of the growth of *P. ellipsoidea* strain Obi and the Obi-derived variants including strains 5P, JH1011, JH1012 and JH1013 when the raceway culture system is used.
Figure 5B:
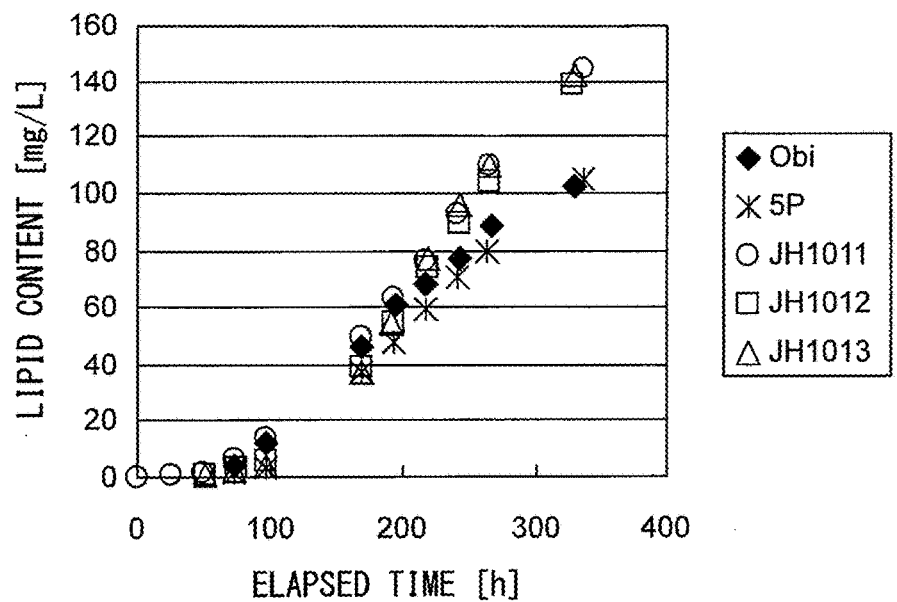
FIG. 5B is a diagram illustrating a graph of the lipid production of *P. ellipsoidea* strain Obi and the Obi-derived variants including strains 5P, JH1011, JH1012 and JH1013 when the raceway culture system is used.

Although the growth rates of strains JH1011, JH1012 and JH1013 were almost equal to that of strain 5P, the lipid contents were relatively high, and as a result, the lipid productivity of each strain increased remarkably (FIG. 5A and FIG. 5B). The lipid productivity (gram) per cultivation period (a day), per culture area ($m^2$) is shown in Table 1 below.

TABLE 1

Lipid productivity per cultivation period, per culture area in cultivation of *P. ellipsoidea* strain Obi and Obi-derived variants: strains 5P; JH1011; JH1012; and JH1013, using the raceway culture system (unit: g/$m^2$/day)

| Obi | 5P | JH1011 | JH1012 | JH1013 |
|-----|-----|--------|--------|--------|
| 1.20 | 1.10 | 1.76 | 1.94 | 2.02 |

As shown in Table 1, as a result of the indoor raceway evaluation, the lipid productivity of strains JH1011, JH1012 and JH1013 increased by up to 68% and 84% compared to the wild-type strain and strain 5P, respectively.

(Example 2) Genome Analysis of Strains JH1011, JH1012 and JH1013

In order to know which genetic mutations induced the improvement of the lipid productivity observed in strains JH1011, JH1012 and JH1013 isolated in Example 1, the genomes of the three strains were analyzed (resequencing) by Illumina HiSeq paired-endsequencing. The resequencing results were matched on the *P. ellipsoidea* strain Obi genome sequence, which has already been established, to create maps using the ELANDv2 software. The information on the *P. ellipsoidea* strain Obi genome sequence also includes the positions of the exons and the introns of the genes which were predicted from the sequence information obtained by the RNA-seq. Based on the information, the mutated genes of strains JH1011, JH1012 and JH1013 were analyzed by comparing with the genome sequences of strain Obi and strain 5P, which is the direct parental strain of strains JH1011, JH1012 and JH1013.

Table 2A and Table 2B below show the analysis results of the comparison of the genome sequence of strain JH1013. In this regard, Table 2B continues from Table 2A.

TABLE 2A

Genetic Mutations Detected in Strain JH1013
The annotation was conducted based on the results of the Blast search through the Swiss-Prot protein database and the motif search using the InterPro. CDR is a coding region; UTR is an untranslated region; and intergenic is a space between two genes.

| 1 | CDR | NS | Leu zipper containing protein |
| 2 | UTR | | Saccharopine dehydrogenase |
| 3 | UTR | | Putative uncharacterized protein |
| 4 | CDR | NS | DYRK |
| 5 | intron | | NADP-dependent Aldo/keto reductase |
| 6 | Intron | | Pyrophosphate-energised proton pump |
| 7 | UTR | | Putative uncharacterized protein |
| 8 | CDR | NS | Putative uncharacterized protein |
| 9 | CDR | NS | Short-chain dehydrogenase/reductase |
| 10 | UTR | | Putative uncharacterized protein |
| 11 | intron | | Riboflavin synthase |
| 12 | CDR | NS | Putative uncharacterized protein |
| 13 | UTR | | Heat-shock protein 70 |
| 14 | UTR | | CRC-domain containing protein (DNA-binding motif) |
| 15 | intron | | Putative uncharacterized protein |
| 16 | CDR | S | Sacsin: cochaperonin |
| 17 | Intron | | Major facilitator superfamily protein |
| 18 | CDR | S | Ribulose bisphosphate carboxylase, small chain |
| 19 | UTR | | F-box/LRR-repeat protein 15 |
| 20 | Intron | | Intron-binding protein |
| 21 | Intron | | Probable serine/threonine-/dual specificity protein kinase, catalytic domain |
| 22 | UTR | | No similar proteins in the database |
| 23 | UTR | | No similar proteins in the database |
| 24 | intron | | No similar proteins in the database |
| 25 | intron | | Chitin synthase |
| 26 | intron | | Outer dynein arm protein 1 |

TABLE 2A-continued

Genetic Mutations Detected in Strain JH1013
The annotation was conducted based on the results of the Blast search through the Swiss-Prot protein database and the motif search using the InterPro. CDR is a coding region; UTR is an untranslated region; and intergenic is a space between two genes.

| 27 | UTR |  | Syntaxin-61 |
| 28 | intron |  | Conserved hypothetical protein |
| 29 | UTR |  | Probalbe endonuclease/exonuclease/phosphatase family protein |
| 30 | intron |  | TBC-domain-containing protein; |
| 31 | UTR |  | Acyl-CoA N-acyltransferase; |
| 32 | Intron |  | Cytochrome b6-f complex subunit 4 |
| 33 | UTR |  | Putative uncharacterized protein |
| 34 | intron |  | Cation-transporting P-type ATPase |
| 35 | intron |  | Alpha/beta-hydrolase |

TABLE 2B

| 36 | intron |    | Putative uncharacterized protein |
| 37 | CDR | NS | 3-Phosphoinositide-dependent protein kinase 1 |
| 38 | intron |    | Protein with an armadillo-type fold |
| 39 | UTR |    | DnaJ-domain-containing protein; |
| 40 | CDR | S  | Oxysterol-binding protein 9 |
| 41 | UTR |    | Glycosyltransferase-like protein |
| 42 | intron |    | Hypersensitive-induced response protein |
| 43 | UTR |    | Putative uncharacterized protein |
| 44 | intron |    | Putative uncharacterized protein |
| 45 | CDR | S  | Brix-domain-containing protein |
| 46 | CDR | NS | Glycoside hydrolase |
| 47 | intron |    | GTP-binding elongation factor family/TypA subfamily |
| 48 | intron |    | Basic leucine-zipper containing protein |
| 49 | intron |    | Uncharacterized chloroplastic protein |

The genome sequence of strain JH1013 covered 98.7% of the genome sequence of *P. ellipsoidea* strain Obi, and 54 base substitutions were detected in the covered region. Five mutations of the 54 substitutions were in the regions which are not transcribed (such a region was defined as an intergenic region). The remaining 49 mutations were in the regions where transcription had been observed (such a region was defined as a gene). The functions of the mutated genes were predicted considering the results of the Blast search through the Swiss-Prot protein database and the results of the motif search using the InterPro.

As a result, with respect to the mutations in the 45 genes, only 11 genes had mutations in their amino acid-encoding regions (CDR). Seven of the 11 genes had mutations which altered the amino acid residues (non-synonymous mutations). Of these seven genes, the genes that remained as candidate causative genes for the improvement of the character of strain JH1013, namely the lipid productivity, were six genes: a Leu zipper containing protein gene, which may be a transcription factor; a DYRK gene, which is believed to be involved in the signal transduction; 3-phosphoinositide-dependent protein kinase gene; and three genes with unknown functions.

Strain JH1011 was analyzed in the same manner. Although 100 mutations were detected in this strain, mutations which altered the amino acid residues were detected only in 11 genes. When three genes with unknown functions which were annotated as predicted proteins were excluded, no genetic mutation which could explain the improvement of the lipid productivity was found in any of the 11 genes. However, a mutation which prevents splicing was found in the exon outside the CDR of the DYRK gene, and it was expected that the mutation repressed the expression of the DYRK gene to a considerable degree.

Strain JH1012 was analyzed in the similar manner. Also in this strain, of the 102 mutations detected, mutations which altered the amino acid residues were detected in eight genes. When three genes with unknown functions which were annotated as predicted proteins were excluded, the only remaining candidate mutated genes, which could explain the improvement of the lipid productivity, were the DYRK gene and a protein kinase gene belonging to another family.

From the above results, mutations which impair the DYRK activity were found in all of strains JH1011, JH1012 and JH1013. The *P. ellipsoidea* genome includes about 10,000 genes. About 100 mutations were introduced to each of strains JH1011, JH1012 and JH1013. Thus, the probability that a mutation is introduced at random to the DYRK gene in strain JH1011, JH1012 or JH1013 is $\frac{1}{100}$, and the probability is one in million that the three strains would all have a mutation in the DYRK gene at the same time.

When spontaneous mutations which affect the amino acid sequences of proteins are considered, about 10 such mutations have been introduced to each of strains JH1011, JH1012 and JH1013. Accordingly, the probability is one in billion that the three strains would each have a mutation which alters the amino acid sequence of the DYRK by chance.

Upon the above consideration, it was concluded that the mutations which contributed to the improvement of the lipid productivity of strains JH1011, JH1012 and JH1013 were the mutations in the DYRK having the amino acid sequence of SEQ ID NO: 3 encoded by the RNA including the nucleotide sequence of SEQ ID NO: 2 transcribed from the gene including the nucleotide sequence of SEQ ID NO: 1. The mutations in the DYRK genes of strains JH1011, JH1012 and JH1013 are shown in FIG. 6A to FIG. 6D.

In FIG. 6A, the mutation sites of strains JH1011, JH1012 and JH1013 which were introduced to the DYRK gene sequence of SEQ ID NO: 1 are underlined, and the changes are described at the right end of the respective lines. The mutation of strain JH1011 was the substitution of GT at the 5' end of an intron with AT, and it is believed that splicing of the intron did not occur at the site as a result of the substitution. In strain JH1012, a spontaneous deletion was occurred in an exon region, which resulted in a frameshift. In strain JH1013, a base in an exon region was substituted. As a result, a codon TGC changed to TTC, and the amino acid residue at the site changed from C to F.

Intensive study has been conducted to solve the above problem. It was found that a variant of a green alga having a mutation in the gene encoding the dual-specificity tyrosine-phosphorylation regulated protein kinase (DYRK: Dual-specificity tYrosine-phosphorylation Regulated protein Kinase, referred to as "DYRK") on the genomic DNA has excellent lipid productivity compared to that of the parental strain or the wild-type strain, and the present disclosure has been completed.

As an example, the present disclosure includes the following.

(1) A green alga variant having a reduced DYRK activity, in which the lipid production per unit time and per unit culture area is improved compared to that of a parental strain, and the DYRK is a protein which has an amino acid sequence with at least 50% sequence identity with the amino acid sequence of an active site and a substrate recognition site of SEQ ID NO:4 and which has a DYRK activity.

(2) The green alga variant according to (1), which is a green alga in which a gene encoding a DYRK has been disrupted.

(3) The green alga variant according to (1), in which the DYRK activity is reduced by the reduction of the expression of a gene encoding a DYRK.

(4) The green alga variant according to (1), in which the DYRK activity is reduced by the reduction of the translation efficiency of a gene encoding a DYRK.

(5) The green alga variant according to any one of (1) to (4) which belongs to Trebouxiophyceae.

(6) The green alga variant according to (5) which belongs to *Coccomyxa* or *Pseudococcomyxa*.

(7) A lipid production method, comprising a step of culturing the green alga variant according to any one of (1) to (6).

According to one example of the present disclosure, it may be possible to produce a green alga with improved lipid productivity. Also, by culturing the variant of the green alga according to the present disclosure, it may be possible to considerably reduce the production cost of a lipid used for a biofuel or the like.

While the embodiment, the configuration, and the aspect of the present disclosure are exemplified, but the embodiment, the configuration, and the aspect according to the present disclosure are not limited to each of the embodiment, configuration, and aspect. For example, an embodiment, a configuration, and an aspect which are obtained by appropriately combining technical parts disclosed in each of different embodiment, configuration, and aspect are also included in the scope of the embodiment, the configuration, and the aspect according to the present disclosure.

What is claimed is:

1. A green alga variant comprising:
a genetic variant of a gene encoding a dual-specificity tyrosine-phosphorylation regulated protein kinase (DYRK), an activity of the DYRK being lost or reduced compared to an activity of DYRK activity of a parental strain,
wherein:
the green alga variant belongs to *Pseudochoricystis ellipsoidea*;
the green algae variant has an increase of a total amount of a lipid production per unit time and per unit culture area compared to a total amount of a lipid production of the parental strain;
a dual-specificity tyrosine-phosphorylation regulated protein kinase of the parental strain is a protein having an amino acid sequence with at least 50% sequence identity with the amino acid sequence of an active site and a substrate recognition site of SEQ ID NO: 4, and having the dual-specificity tyrosine-phosphorylation regulated protein kinase activity; and
the green alga variant is generated by:
contacting genomic DNA encoding for a DYRK in the parental strain with a mutagenic substance to generate a plurality of genetic variants;
screening the plurality of genetic variants for genetic variants having increased lipid content; and
isolating the green alga variant having a genetic variant of the gene encoding the DYRK from the genetic variants having increased lipid content.

2. The green alga variant according to claim 1, which is a green alga in which the gene encoding a dual-specificity tyrosine-phosphorylation regulated protein kinase is disrupted.

3. A lipid production method, comprising:
culturing the green alga variant according to claim 1.

4. The green alga variant according to claim 1, wherein:
the gene encoding the dual-specificity tyrosine-phosphorylation regulated protein kinase has either a nucleotide substitution mutation or a nucleotide deletion mutation as the genetic variant.

5. The green alga variant according to claim 1, wherein the genetic variant of the gene encoding the DYRK comprises a base substitution in an intron that results in a splice variant, a base substitution in an exon that results in an amino acid mutation, or a deletion in an exon that results in a frameshift mutation.

* * * * *

SEQUENCE LISTING

```
<160> NUMBER OF SEQ ID NOS: 7

<210> SEQ ID NO 1
<211> LENGTH: 9234
<212> TYPE: DNA
<213> ORGANISM: Pseudochoricystis ellipsoidea

<400> SEQUENCE: 1
catttcaatc caaaaaagag aaggatagag agttgcgaag atggtctgtg catgcaagtt      60
gttttgatca cgatgttgct gtcataggtt gcgaggtaga agttgcttcc agaatattgc     120
ttctcatcat ctggcttgta cttttgtgtg catgctgaga acatagctct gaaaccgatg     180
agttaccata tgctcataat ctgcgccgat gcatcctctg acaggcagat tgatccaagt     240
tggccagcca tagtcttctt gaaagagagg aagaactgtg ctgtgaagtt gttatctagc     300
ggttgaagcg atctggctct aagggcacgg atagacgaga agacatcgtt caaatcctag     360
gtgcgttgca tatatttccc gcttagcctc ccaggagcat ttctaaaacc caagattgtt     420
cacgacacca ggcaacactg atgctacttc aacaagcgtg ggcaatgcca cattttgatt     480
ttcttgcagc tgtatcctct acggtgtgat ttcttctcat atgttggcag gacgtgcatc     540
gcctcaggtc tgactcgatg gacaaccaaa gctcaggcac ctccagggc atggaaagga      600 ggtgtctgac tgttccgggc ttgggaaaag gcaacgaagg ctttgacaac gaaaataacg     660
acctcatatt gtatgtggat gacgtccttt ccgtgaaaga aaggaggtgt gttgcttttc     720
ctctcatttc tgtgcctgtg aggattatac ttgctcggca gacgagcacc cgcggcatct     780
gaatctactc ttagttccac tcatggtgag tattcttagt gcttattcga cgctcttcct     840
cattcacagg tacattgtca gggatatgct gggccaaggc accttcgggc aggtcgtgcg     900
atgccttcga gaggatagcc gtgaggaagt ggctgtgaag tcattaaga atcaaactgc      960 cttctatcat caggtcagta gggcattgaa gggcggctta ttccctcgtc cgtgtactga    1020
tcgttcttag cttgttttct tcggcatccg ttgtccgagg ggcctgctcg ccgctgatgg    1080
catgtggctc tgtatagcca gtagtgatgc tagtctgtct atgcaggctc gtgtcgaggt    1140
gggcgtcctg cagtttctga acacccgggg ggatccagag aacaggcatc acatcgtgag    1200
gatgcgcgac ttctttctgt tccgtaacca tctctgcctc gtgttcgagc tcttgagcgt    1260
caacctgtac gagctcgtca agcacaacca gttcagggc ctgtctatga acctcctgcg     1320
cgttttcatc agccaggtac agaagatcct agtgacacag cacctgatat tgggacactg    1380
cggccctcca ggcccagtg cactcacgtg gtgttgcgct tgtctttgca gtatattgta     1440
gcactcctct gcagctttct ggatgctccc aattacacca gtaaggatat taccttcctc    1500
```

```
gcgtctccct ctgtcaccta cttgtgcagg gtcatgcacc aacacaggcg tctgtgtgtt      1560
ttgacatgtc taagattaca agctcgtgtg ctgttctgca gatcttggac gcactgtcag      1620
tgctccatga atgcaacatt atccactgcg atctcaagcc ggagaacgtg ctgctcaagg      1680
gactagactc gggggaaatc aaagtcatcg acttcgggtc agcttgcttt gagaatcgca      1740
ccatgtactc ctacatccag tcacggttct accgctcccc ggaggtgacc gtcccagcac      1800
tgtcagacct tccagccttt ctagtatgat tgatcttcaa ggaagcactt ctggctgctg      1860
tccttgtggc atacttagtt cattaattcc atgcagcgtc ccacctcagt tcttcctttt      1920
tgaaagacag caatctcagt ggcttgaaca gggtggagca aacttggtgt agagcactgc      1980
ctgttctcaa tgactgtgcc tgatggaagc agccataaga aacttgtttg tggtgccagg      2040
tgctgctggg gtaccatat gatgtggcca ttgatatgtg gtcactgggc tgcatggcgg       2100
ctgagctcta cctgggtttg cccttgtttc cgggcgcctc ggagcacgat ctcctggtgc      2160
gcatcgtgga gatgctggga atgcctccac cacatgtgct ggcacgcgca cagcacctgc      2220
gcaaatactt caagcgcgag gaggaagtcc tgaatgtggg aggcgtcccc atgcgccgcc      2280
agaagtaccg agtgagcctt ccctggttg accctgcaaa gttcagcaag ggagacgatg       2340
cgatgtacac cttgtcagtc tgacaagatt atgggtgatc ttgtcagact gcacaagtgt      2400
acctcacatc gtctgccttg catgcgagtg taatgggcga ggagttcagc agacattgtg      2460
atcttccttg cacaacatgc attcgatctg tcagacatcg cctgccgcac ctcgaccaat      2520
gtatgtgctc tctttcatac cttgggtgta cctcagatgt cgggtccgtg aaaaagtata     2580
accaggtcct gatgccagac gcacgtgttg tggcagctgc gcacacaggc agagttcgag      2640
gcgatgcaga atgtgaaggc gcctgccggc aaacgctact tccagcacac caagctgccg      2700
gacatcatcg gcgcgtaccc cttccgatcg gggctcaccg aggcgcagca ggcgcatgag      2760
accgagcggc gcgaggcctt cctcgatttc ctcatgggtg tcctggtgcg tacctctgca      2820
ccgggggatt cagcatgcaa taaatgggtg tttggttctg gctgagcacg agatattgag      2880
gccgtgaaat gcaccacggt ctggagaata tcacatgttg gggcttcaca ccttcatcat      2940
tgtctaaaca ggacctggac ccagaggtgc gctggagccc gcagcaggcg ctgcagcatc      3000
cattcctcac aggggcgcgt ttcacggggc cattccagcc gccaccgcgc gtgcatgtgc      3060
gcgctcggcc ggccgccgcg ccgcgctcgg ccccgacgg ctcgggcgtg atgtcgccct       3120
acaactccgc actgtacaac tcccccgtgg ccaccatgct ggccacatcc cccgagttcc      3180
atgcgcaggc gcatgctgca gcaatggctg ctgtgcaggc acgcgccctt cttgatattg      3240
ccaaggtgtc atgcgcagaa atgtgtgttg aatattatgc atgatggcac ctggttggtt      3300
gccaccatgg aggacaaagt cgacgttgaa accggacaaa gtggcaagtc attggcactt      3360
tcgttgtttc aatgtagact ttgtcctcgt tgtctgtggc tgtgcagacc cacgttgttt      3420
tagcatcctt taaagagagc ttctggaggc tccacggtct tggctcagtc ctgcaacaga      3480
ttgtgacttt gccatgcagc atgtttcaaa tgcctacaga aattgcattg attttgatac      3540
aaacaaatca gcttttagtg cttcctgacg tgcttgatgg cattctacag gcgcatttca      3600
gcccgcgggg agcgggcgct cttggggcca gcttgggcgc tccacagcag cagaattcct      3660
tcgagccggc catcgcggtg gcttccgccc tggccgccgc acagtacaac ggcatccagc      3720
agcaggtgcc tggcctcgtt ttacccccct gtattagaat tgcaaaaact gcctggttag      3780
ataatcactc cttttcaatg gcagtatcga gtgggtgatg acggggctgc tggtggcaga      3840
atggcatgca gcagcacacg ccggccgatc gtgcgcagca ggcgcaatat cagcacagcg      3900
```

```
gggctgtgca catacagcag caggcgctgc atgggatgca gtatggctcc tttgaccta      3960
tgtatgccag cggacaccac agctcgagcc aggtggggct gcttccaagc ctctcttaga    4020
tatggtactc aactgcagct gcattttcga gaagctgctc attcatgtgc tttctctcga    4080
gcgctcttgc atgggcttgt tgttctcttg cagtgagctt ctcgagatga aatgttttg     4140
ctggcattcc tggtaatgag ggctgtcggg aaaaaacaaa ttaaatttgt cgagattggg    4200
gtcagcctaa agtatcatat tttctagggg tcagagggtt tcacttacta tcttggcttc   4260
aataacaatt ctcttctctc gtcttacgcg tggtttgatt gcttgatgtc ttgcagcaga   4320
cagacacccc atatggaacg ccctacgggt ccttcagtgg gggttccttc agctcactga   4380
gcagcatgca gacgccgccg cactcgctca gcggctactc gcccatgacc cacctccatg   4440
gcctgcccag ctcctatcac agcacacccg gccgctctgg cgccatgct ggctcactgc    4500
aggtgctgtt ctagctattg cagtaaaaaa tgggtgtttt ggtggaagga tgcactcttt   4560
tgtgatcttc gtgttgtggg agggaaatac gccctggcca gctatcctgt ttttttaac    4620
agatgagatt gcaggtccca gaccttggcg tgtcatatta ctgtgtttca agaggcatga   4680
ttgtctgatc aacagcacct tctcattcag caggaccacc gcaagcaaga agagcagctt   4740
catacaacat gcctgttctg aacactctgg aaatgtacag ggcacgccca tggcgaccctc  4800
ttacaacagc tactcgtatc tggcggcggc tgccgcggcg gcctcggcgc agcaggcggc   4860
acagcagccg gtggtgggct ctctggagac gctgcgcgca aacgccatgt ggaatctgcc   4920
ccatggcccc gccttcctga atggacagcc caacgccgcc tacctgggca ctcccatgc    4980
ccggtgcgtt ctcagtcaac tcagaaagtt tctctttcat atacttgctc cttctgcgca   5040
cccatggatg atgattactg caaggctacc atcactgact ttgctatgca gtgttggtgc   5100
caattggtcc ccacgagagc tgataacggc ccctgaacag caaggtcccc aggggcataa   5160
accatattgg agttggtgaa agtgcctaag ggcctactga tgggcctcat aatcacaaag   5220
ctcattgggg tgcctgctcg tgagcaggat cggcagcggt gcattggcg acggcatgtt    5280
gggtagcctg cccagggaga acctcctggg caccctccaa gacgcagacc accacggggc   5340
gcagcaagca gcagacaaac gcgccaattc aggcccatgc gccagctcag cggagatggc   5400
agcgtgctca ctgggcaact atgcaggaaa cgtgctccca gacgggccgg cacagcagca   5460
gcagcgcttg gaccccagc agcagtcctg gcactccttt acacagtccc tgcagcagtg   5520
cacctcgccg cagcaggaca ggcatagcaa tactgcagga atcgagctcc cacctggcgc   5580
gtctaacgga gtatccagcg cacagcaagg cagtgcagcg gagcagcagc agcggggggc   5640
ccatcggcca gaacaggcaa cagagagaca acagccagat caggcacggc tgcccccgga   5700
gcacctgccg ccgaaagagg ccaccagcag aagggtgctc acctatgagg agcacctccg   5760
agaggaggag ctcaaggcgc agctggccga gcgcactggt gggtcgtctg ccgagataac   5820
acatcctggc cccctattg cacagctgct cacgctcata cgggacat gtccgccatc      5880
tgccagcata ctcgtgtcag gatgcatgct gactggtgta acatgccacc tccggcccgt   5940
cccgagtgag aagcacttcg attctgcaat gggtaccact gggtctcagg tgtaccataa   6000
ccgtggtttt aaaatgttac aaagaagaag aagaagatta cccatcattc cagccgccca   6060
tcattccagc tgcctagggt tgatcagatg acccacaacc acccgcagaa ttcttcaaca   6120
cagcaaaaca agcctgtatg aaacgagcaa cctcaacaat gtcctcctgc acatgaaag    6180
cctgcatagt taagggtgac gtctgactgc acgtgctaat gcgtcaggtg gtgaagctgc   6240
```

```
agagggcact gggcgggggg cgccggctgc aagcgcaggc aacggggcgg catccttgtc   6300
ggagggccgc acaaacatgt cgcgcacgca ctcacaggat gttggcccca cacccagcga   6360
ctgggacccc agctacaggt ctggcgccca ccttgccccc tgatcacgtt tctgtcctgc   6420
ttgttgagct tcctcgtggg atgctctcgt ggccctgctc tgatctgggc agtccttcct   6480
actggatggt gctgttcctc ctggatgtca agatgcgaag atagattcat ctgaaaggat   6540
ttgtcaggac tgtatttgtc tggccaccct cattacagcg ggtcgccatg gccagcactg   6600
gttcttgctg cctgctgcag caaatggctg ccagcaaacg atcgctcgct ggacagtgca   6660
ccttcatgca gttctcctgc cgatccattt tgcggtaccg caaaatggat cggcatcaag   6720
aaagcaggag aattgtacaa agctgcgctc atccagctgg catttggctg gcagccattt   6780
gctgcagcac agccaactga ttggcatcaa tggtgtccag tcttgcatgc cccattaact   6840
tgtggtgtac cagcttctca catgtcattt gcattataat agtaatgcta gctaccgtga   6900
ttgctcgctg atcctagcgc tgtgctgtgt acatgtgcag tgatgaccag ctcctcgatg   6960
atgcgggatg ggccaggttc cccgacggcc gcgctcggca aagcgcgcga agcgcgctgc   7020
tgccgcgctt tgccgacacg gccgccgccg cggccaccga tgcggcgggg gggcccgcgc   7080
agccgcagct tcccggcagc tatgcggagt cactcacgtc gccggtgcag ccatcgccgc   7140 agggcccta cgacacgcac tggctgcgct gcaatgggga tgccgctctc cggcacgccg   7200
ccgcagacac gcccctctcg gtgcgcctaa cctggctctc cgctgcatct ttctgggcag   7260
agtgtctact ctgactgcgt tccttctttc tccgtttctc tcctacttct gtttctttgt   7320
aatctttctt cgtagtgttc gttgtgatgc agtcactgct ttgtttgttt gcttcttcat   7380
gctgttcatg ttggtggttg acatgtcact gcttgaagga gtggtgccgt gtatgtgctt   7440
tcagccatgg aatgtgtttg tacaaatgct gagaatagct catgaatgac acaggcattc   7500
taaggtgtgt ttctgtctgg ggctgcagat gctaccgggc tcgttgatac ccaaagcgcc   7560
ctacacaagc atcggtttcg cccccggcaa gagatcggc tgcaattgag ttgacctga   7620 gcagatgtca acagccgcat tgcggcaagg ggcatctgct tctgatctct ggggcgctca   7680
ttttgggggc agtcgaggac aatgctgttg tggcaggcac caacaaaggt gcattgaaga   7740
ggttcttcac ccatggatca aggcatgcca catggtcttt tgcctgcaca ctaggatcac   7800
agtctgatgg ctgtggatcc cttactgctg ctgctgccca tatctcaatt gggtggaagg   7860
caagcggtgg caggctcgag tgtaaagaga gggagagagg gagagagctc gctgcttgat   7920
gtggtcgcag ctgtggcttg gggcttgcac ttattcgtgt tgcaaattcc tatcacatgt   7980
cagggcatgg acatactggc attgatcagt gatgaggtgc actgccaaag gtgccactgg   8040
cagtggagcg tcggctctgg accaaggttt ggcaccaatt tttactcttc atggtgtgta   8100
gtgaggtaga ctctgtctct gcgggtgcat gtatgtttca gtctgtttgt gagcgcgagt   8160
ggccttgtga gtagtgagca ttattacttg atctgtgagg tttgggccca gagtagcagt   8220
tctttggcca tattggaggt catgactgca gtagatagat ggacctgtga accttccttg   8280
ttgttcctag ctaaccgcgc tgcattgcat gctgcctgca ttttatgtag tctcagtcaa   8340
cgtagatata tcatttgggg ctttaagtca caagcgggca gcaccagagg tcctggcttg   8400
ttgaccttgc tgtgaagtac cgaaaacttc caaaagccct ggatttctcc cctggctgat   8460
gatagaatca cacagcctca tgagtgatca ctgcaacatg ccggttggaa tacagtgaaa   8520
gcatttttcg gtgccaatgt aacgagtgtt ggaagttgaa atgtgatcac agtgcactca   8580
tcagagcacc attgacctgc gcccagacag ccttgtaagc tcttggcatg agtggcttca   8640
```

```
gtcctaggag gcctgaaatc ttaaatgcct atggtatcac cggtggcatg tacatgtgac      8700
aactattcac cgtgagtcac tgtgcataat accatcactg atcacacgac ctgcatcacg      8760
caacagccat gctctttaca ctgcagtggc tgcgcagctg caaatatata tcagcagtaa      8820
tcatcattgt caaaggtttg ctgtcttttg atgagcatga attaacaatg acagcatagg      8880
tctctccaga aagaaagcac ttgatgcaga aggttgcaac ctgaaacctc atcagtcagc      8940
tgcatacatt gtgactgtac acatccaacg gaaacatgca cacaccaccc cagcaattcc      9000
aagagaaagt tcctttggga taataaatca ctgcccgata aagctttgtc acacgcacag      9060
tgcaattgac agtcatactg tatgtagcaa agcgcaactt tagcccggtg tattttgttg      9120
cggacttctc tacactgtac aaaccttgta caactcaacc taaggcacaa tgctacactg      9180
gtgatgcaca tgcaaagctt aaacagcatc agagtcagct cagccaggtc acac          9234

<210> SEQ ID NO 2
<211> LENGTH: 5561
<212> TYPE: RNA
<213> ORGANISM: Pseudochoricystis ellipsoidea
<220> FEATURE:
<221> NAME/KEY: CDS
<222> LOCATION: (388)..(3495)

<400> SEQUENCE: 2
cauuucaauc caaaaaagag aaggauagag aguugcgaag auggucugug caugcaaguu      60
guuuugauca cgauguugcu gucauagguu gcgagguaga aguugcuucc agaauauugc      120
uucucaucau cuggcuugua cuuuuguguc caugcucgaga acauagcucu gaaaccgaug      180
aguuaccaua ugcucauaau cugcgccgau gcauccucug acaggcagau ugauccaagu      240
uggccagcca uagucuucuu gaaagagagg aagaacugug cugugaaguu guuaucuagc      300
gguugaagcg aucuggcucu aagggcacgg auagacgaga agacaucguu caaauccuag      360
gacgugcauc gccucagguc ugacucg atg gac aac caa agc uca ggc acc ucc     414
                                Met Asp Asn Gln Ser Ser Gly Thr Ser
                                1               5 agg ggc aug gaa agg agg ugu cug acu guu ccg ggc uug gga aaa ggc       462
Arg Gly Met Glu Arg Arg Cys Leu Thr Val Pro Gly Leu Gly Lys Gly
10                  15                  20                  25 aac gaa ggc uuu gac aac gaa aau aac gac cuc aua uug uau gug gau       510
Asn Glu Gly Phe Asp Asn Glu Asn Asn Asp Leu Ile Leu Tyr Val Asp
                30                  35                  40 gac guc cuu ucc gug aaa gaa agg agg uac auu guc agg gau aug cug       558
Asp Val Leu Ser Val Lys Glu Arg Arg Tyr Ile Val Arg Asp Met Leu
            45                  50                  55 ggc caa ggc acc uuc ggg cag guc gug cga ugc cuu cga gag gau agc       606
Gly Gln Gly Thr Phe Gly Gln Val Val Arg Cys Leu Arg Glu Asp Ser
        60                  65                  70 cgu gag gaa gug gcu gug aag guc auu aag aau caa acu gcc uuc uau       654
Arg Glu Glu Val Ala Val Lys Val Ile Lys Asn Gln Thr Ala Phe Tyr
    75                  80                  85 cau cag gcu cgu guc gag gug ggc guc cug cag uuu cug aac acc cgg       702
His Gln Ala Arg Val Glu Val Gly Val Leu Gln Phe Leu Asn Thr Arg
90                  95                  100                 105 ggg gau cca gag aac agg cau cac auc gug agg aug cgc gac uuc uuu       750
Gly Asp Pro Glu Asn Arg His His Ile Val Arg Met Arg Asp Phe Phe
                110                 115                 120 cug uuc cgu aac cau cuc ugc cuc gug uuc gag cuc uug agc guc aac       798
Leu Phe Arg Asn His Leu Cys Leu Val Phe Glu Leu Leu Ser Val Asn
            125                 130                 135
```

```
cug uac gag cuc guc aag cac aac cag uuc agg ggc cug ucu aug aac     846
Leu Tyr Glu Leu Val Lys His Asn Gln Phe Arg Gly Leu Ser Met Asn
        140                 145                 150 cuc cug cgc guu uuc auc agc cag auc uug gac gca cug uca gug cuc     894
Leu Leu Arg Val Phe Ile Ser Gln Ile Leu Asp Ala Leu Ser Val Leu
    155                 160                 165 cau gaa ugc aac auu auc cac ugc gau cuc aag ccg gag aac gug cug     942
His Glu Cys Asn Ile Ile His Cys Asp Leu Lys Pro Glu Asn Val Leu
170                 175                 180                 185 cuc aag gga cua gac ucg ggg gaa auc aaa guc auc gac uuc ggg uca     990
Leu Lys Gly Leu Asp Ser Gly Glu Ile Lys Val Ile Asp Phe Gly Ser
                190                 195                 200 gcu ugc uuu gag aau cgc acc aug uac ucc uac auc cag uca cgg uuc    1038
Ala Cys Phe Glu Asn Arg Thr Met Tyr Ser Tyr Ile Gln Ser Arg Phe
        205                 210                 215 uac cgc ucc ccg gag gug cug cug ggg uac cca uau gau gug gcc auu    1086
Tyr Arg Ser Pro Glu Val Leu Leu Gly Tyr Pro Tyr Asp Val Ala Ile
    220                 225                 230 gau aug ugg uca cug ggc ugc aug gcg gcu gag cuc uac cug ggu uug    1134
Asp Met Trp Ser Leu Gly Cys Met Ala Ala Glu Leu Tyr Leu Gly Leu
235                 240                 245 ccc uug uuu ccg ggc gcc ucg gag cac gau cuc cug gug cgc auc gug    1182
Pro Leu Phe Pro Gly Ala Ser Glu His Asp Leu Leu Val Arg Ile Val
250                 255                 260                 265 gag aug cug gga aug ccu cca cca cau gug cug gca cgc gca cag cac    1230
Glu Met Leu Gly Met Pro Pro Pro His Val Leu Ala Arg Ala Gln His
                270                 275                 280 cug cgc aaa uac uuc aag cgc gag gag gaa guc cug aau gug gga ggc    1278
Leu Arg Lys Tyr Phe Lys Arg Glu Glu Glu Val Leu Asn Val Gly Gly
        285                 290                 295 guc ccc aug cgc cgc cag aag uac cga cug cgc aca cag gca gag uuc    1326
Val Pro Met Arg Arg Gln Lys Tyr Arg Leu Arg Thr Gln Ala Glu Phe
    300                 305                 310 gag gcg aug cag aau gug aag gcg ccu gcc ggg aaa cgc uac uuc cag    1374
Glu Ala Met Gln Asn Val Lys Ala Pro Ala Gly Lys Arg Tyr Phe Gln
315                 320                 325 cac acc aag cug ccg gac auc auc ggc gcg uac ccc uuc cga ucg ggg    1422
His Thr Lys Leu Pro Asp Ile Ile Gly Ala Tyr Pro Phe Arg Ser Gly
330                 335                 340                 345 cuc acc gag gcg cag cag gcg cau gag acc gag cgg cgc gag gcc uuc    1470
Leu Thr Glu Ala Gln Gln Ala His Glu Thr Glu Arg Arg Glu Ala Phe
                350                 355                 360 cuc gau uuc cuc aug ggu guc cug gac cug gac cca gag gug cgc ugg    1518
Leu Asp Phe Leu Met Gly Val Leu Asp Leu Asp Pro Glu Val Arg Trp
        365                 370                 375 agc ccg cag cag gcg cug cag cau cca uuc cuc aca ggg gcg cgu uuc    1566
Ser Pro Gln Gln Ala Leu Gln His Pro Phe Leu Thr Gly Ala Arg Phe
    380                 385                 390 acg ggg cca uuc cag ccg cca ccg cgc gug cau gug cgc gcu cgg ccg    1614
Thr Gly Pro Phe Gln Pro Pro Pro Arg Val His Val Arg Ala Arg Pro
395                 400                 405 gcc gcc gcg ccg cgc ucg gcc ccc gac ggc ucg ggc gug aug ucg ccc    1662
Ala Ala Ala Pro Arg Ser Ala Pro Asp Gly Ser Gly Val Met Ser Pro
410                 415                 420                 425 uac aac ucc gca cug uac aac ucc ccc gug gcc acc aug cug gcc aca    1710
Tyr Asn Ser Ala Leu Tyr Asn Ser Pro Val Ala Thr Met Leu Ala Thr
                430                 435                 440 ucc ccc gag uuc cau gcg cag gcg cau gcu gca gca aug gcu gcu gug    1758
Ser Pro Glu Phe His Ala Gln Ala His Ala Ala Ala Met Ala Ala Val
```

-continued

|     |     |     |     | 445 |     |     |     | 450 |     |     |     | 455 |     |     |      |
|-----|-----|-----|-----|-----|-----|-----|-----|-----|-----|-----|-----|-----|-----|-----|------|
| cag | gcg | cau | uuc | agc | ccg | cgg | gga | gcg | ggc | gcu | cuu | ggg | gcc | agc | uug  | 1806 |
| Gln | Ala | His | Phe | Ser | Pro | Arg | Gly | Ala | Gly | Ala | Leu | Gly | Ala | Ser | Leu  |
|     | 460 |     |     |     |     | 465 |     |     |     |     | 470 |     |     |     |      |

```
cag gcg cau uuc agc ccg cgg gga gcg ggc gcu cuu ggg gcc agc uug     1806
Gln Ala His Phe Ser Pro Arg Gly Ala Gly Ala Leu Gly Ala Ser Leu
    460                 465                 470 ggc gcu cca cag cag cag aau ucc uuc gag ccg gcc auc gcg gug gcu     1854
Gly Ala Pro Gln Gln Gln Asn Ser Phe Glu Pro Ala Ile Ala Val Ala
475                 480                 485 ucc gcc cug gcc gcc gca cag uac aac ggc auc cag cag cag aau ggc     1902
Ser Ala Leu Ala Ala Ala Gln Tyr Asn Gly Ile Gln Gln Gln Asn Gly
490                 495                 500                 505 aug cag cag cac acg ccg gcc gau cgu gcg cag cag gcg caa uau cag     1950
Met Gln Gln His Thr Pro Ala Asp Arg Ala Gln Gln Ala Gln Tyr Gln
                510                 515                 520 cac agc ggg gcu gug cac aua cag cag cag gcg cug cau ggg aug cag     1998
His Ser Gly Ala Val His Ile Gln Gln Gln Ala Leu His Gly Met Gln
            525                 530                 535 uau ggc ucc uuu gac ccu aug uau gcc agc gga cac cac agc ucg agc     2046
Tyr Gly Ser Phe Asp Pro Met Tyr Ala Ser Gly His His Ser Ser Ser
        540                 545                 550 cag aca gac acc cca uau gga acg ccc uac ggg ucc uuc agu ggg ggu     2094
Gln Thr Asp Thr Pro Tyr Gly Thr Pro Tyr Gly Ser Phe Ser Gly Gly
555                 560                 565 ucc uuc agc uca cug agc agc aug cag acg ccg ccg cac ucg cuc agc     2142
Ser Phe Ser Ser Leu Ser Ser Met Gln Thr Pro Pro His Ser Leu Ser
570                 575                 580                 585 ggc uac ucg ccc aug acc cac cuc cau ggc cug ccc agc ucc uau cac     2190
Gly Tyr Ser Pro Met Thr His Leu His Gly Leu Pro Ser Ser Tyr His
                590                 595                 600 agc aca ccc ggc cgc ucu ggc gcc cau gcu ggc uca cug cag ggc acg     2238
Ser Thr Pro Gly Arg Ser Gly Ala His Ala Gly Ser Leu Gln Gly Thr
            605                 610                 615 ccc aug gcg acc ucu uac aac agc uac ucg uau cug gcg gcg gcu gcc     2286
Pro Met Ala Thr Ser Tyr Asn Ser Tyr Ser Tyr Leu Ala Ala Ala Ala
        620                 625                 630 gcg gcg gcc ucg gcg cag cag gcg gca cag cag ccg gug gug ggc ucu     2334
Ala Ala Ala Ser Ala Gln Gln Ala Gln Gln Pro Val Val Gly Ser
635                 640                 645 cug gag acg cug cgc gca aac gcc aug ugg aau cug ccc cau ggc ccc     2382
Leu Glu Thr Leu Arg Ala Asn Ala Met Trp Asn Leu Pro His Gly Pro
650                 655                 660                 665 gcc uuc cug aau gga cag ccc aac gcc gcc uac cug ggc acc ucc cau     2430
Ala Phe Leu Asn Gly Gln Pro Asn Ala Ala Tyr Leu Gly Thr Ser His
                670                 675                 680 gcc cgg auc ggc agc ggu gca uuc ggc gac ggc aug uug ggu agc cug     2478
Ala Arg Ile Gly Ser Gly Ala Phe Gly Asp Gly Met Leu Gly Ser Leu
            685                 690                 695 ccc agg gag aac cuc cug ggc acc cuc caa gac gca gac cac cac ggg     2526
Pro Arg Glu Asn Leu Leu Gly Thr Leu Gln Asp Ala Asp His His Gly
        700                 705                 710 gcg cag caa gca gca gac aaa cgc gcc aau uca ggc cca ugc gcc agc     2574
Ala Gln Gln Ala Ala Asp Lys Arg Ala Asn Ser Gly Pro Cys Ala Ser
715                 720                 725 uca gcg gag aug gca gcg ugc uca cug ggc aac uau gca gga aac gug     2622
Ser Ala Glu Met Ala Ala Cys Ser Leu Gly Asn Tyr Ala Gly Asn Val
730                 735                 740                 745 cuc cca gac ggg ccg gca cag cag cag cgc uug gac ccc cag cag         2670
Leu Pro Asp Gly Pro Ala Gln Gln Gln Arg Leu Asp Pro Gln Gln
                750                 755                 760 cag ucc ugg cac ucc uuu aca cag ucc cug cag cag ugc acc ucg ccg     2718
Gln Ser Trp His Ser Phe Thr Gln Ser Leu Gln Gln Cys Thr Ser Pro
```

-continued

```
                Gln Ser Trp His Ser Phe Thr Gln Ser Leu Gln Gln Cys Thr Ser Pro
                            765                 770                 775 cag cag gac agg cau agc aau acu gca gga auc gag cuc cca ccu ggc      2766
Gln Gln Asp Arg His Ser Asn Thr Ala Gly Ile Glu Leu Pro Pro Gly
            780                 785                 790 gcg ucu aac gga gua ucc agc gca cag caa ggc agu gca gcg gag cag      2814
Ala Ser Asn Gly Val Ser Ser Ala Gln Gln Gly Ser Ala Ala Glu Gln
        795                 800                 805 cag cag cgg ggg gcc cau cgg cca gaa cag gca aca gag aga caa cag      2862
Gln Gln Arg Gly Ala His Arg Pro Glu Gln Ala Thr Glu Arg Gln Gln
810                 815                 820                 825 cca gau cag gca cgg cug ccc ccg gag cac cug ccg ccg aaa gag gcc      2910
Pro Asp Gln Ala Arg Leu Pro Pro Glu His Leu Pro Pro Lys Glu Ala
                830                 835                 840 acc agc aga agg gug cuc acc uau gag gag cac cuc cga gag gag gag      2958
Thr Ser Arg Arg Val Leu Thr Tyr Glu Glu His Leu Arg Glu Glu Glu
            845                 850                 855 cuc aag gcg cag cug gcc gag cgc acu ggu ggu gaa gcu gca gag ggc      3006
Leu Lys Ala Gln Leu Ala Glu Arg Thr Gly Gly Glu Ala Ala Glu Gly
        860                 865                 870 acu ggg cgg ggg gcg ccg gcu gca agc gca ggc aac ggg gcg gca ucc      3054
Thr Gly Arg Gly Ala Pro Ala Ala Ser Ala Gly Asn Gly Ala Ala Ser
    875                 880                 885 uug ucg gag ggc cgc aca aac aug ucg cgc acg cac uca cag gau guu      3102
Leu Ser Glu Gly Arg Thr Asn Met Ser Arg Thr His Ser Gln Asp Val
890                 895                 900                 905 ggc ccc aca ccc agc gac ugg gac ccc agc uac agu gau gac cag cuc      3150
Gly Pro Thr Pro Ser Asp Trp Asp Pro Ser Tyr Ser Asp Asp Gln Leu
                910                 915                 920 cuc gau gau gcg gga ugg gcc agg uuc ccc gac ggc cgc gcu cgg caa      3198
Leu Asp Asp Ala Gly Trp Ala Arg Phe Pro Asp Gly Arg Ala Arg Gln
            925                 930                 935 agc gcg cga agc gcg cug cug ccg cgc uuu gcc gac acg gcc gcc gcc      3246
Ser Ala Arg Ser Ala Leu Leu Pro Arg Phe Ala Asp Thr Ala Ala Ala
        940                 945                 950 gcg gcc acc gau gcg gcg ggg ggg ccc gcg cag ccg cag cuu ccc ggc      3294
Ala Ala Thr Asp Ala Ala Gly Gly Pro Ala Gln Pro Gln Leu Pro Gly
    955                 960                 965 agc uau gcg gag uca cuc acg ucg ccg gug cag cca ucg ccg cag ggc      3342
Ser Tyr Ala Glu Ser Leu Thr Ser Pro Val Gln Pro Ser Pro Gln Gly
970                 975                 980                 985 ccc uac gac acg cac ugg cug cgc ugc aau ggg gau gcc gcu cuc  cgg     3390
Pro Tyr Asp Thr His Trp Leu Arg Cys Asn Gly Asp Ala Ala Leu  Arg
                990                 995                 1000 cac gcc gcc gca  gac acg ccc cuc ucg  aug cua ccg ggc ucg  uug       3435
His Ala Ala Ala  Asp Thr Pro Leu Ser  Met Leu Pro Gly Ser  Leu
                 1005             1010                1015 aua ccc aaa gcg  ccc uac aca agc auc  ggu uuc gcc ccc ggc  aag       3480
Ile Pro Lys Ala  Pro Tyr Thr Ser Ile  Gly Phe Ala Pro Gly  Lys
                 1020             1025                1030 aga ucu ggc ugc  aau ugagguugac cugagcagau gucaacagcc gcauugcggc     3535
Arg Ser Gly Cys  Asn
                 1035 aaggggcauc ugcuucugau cucuggggcg cucauuuugg gggcagucga ggacaaugcu    3595 guuguggcag gcaccaacaa aggugcauug aagagguucu ucacccaugg aucaaggcau    3655 gccacauggu cuuugccoug cacacuagga ucaagucug auggcugugg aucccuuacu    3715 gcugcugcug cccauaucuc aauuggugug aaggcaagcg guggcaggcu cgaguguaaa    3775
```

| | |
|---|---|
| gagagggaga gagggagaga gcucgcugcu ugaugugguc gcagcugugg cuuggggcuu | 3835 |
| gcacuuauuc guguugcaaa uuccuaucac augucaggc auggacauac uggcauugau | 3895 |
| cagugaugag gugcacugcc aaaggugcca cuggcagugg agcgucggcu cuggaccaag | 3955 |
| guuuggcacc aauuuuuacu cuucaugguu uguagagagg uagacucugu cucugcgggu | 4015 |
| gcauguaugu uucagucugu uugugagcgc gaguggccuu ugaguagug agcauuauua | 4075 |
| cuugaucugu gagguuuggg cccagaguag caguucuuug gccauauugg aggucaugac | 4135 |
| ugcaguagau agauggaccu gugaaccuuc cuuguuguuc cuagcuaacc gcgcugcauu | 4195 |
| gcaugcugcc ugcauuuuau guagucucag ucaacguaga uauaucauuu ggggcuuuaa | 4255 |
| gucacaagcg ggcagcacca gagguccugg cuuguugacc uugcugugaa guaccgaaaa | 4315 |
| cuuccaaaag cccuggauuu ucccccuggc ugaugauaga aucacacagc cucaugagug | 4375 |
| aucacugcaa caugccgguu ggaauacagu gaaagcauuu uucggugcca auaacgag | 4435 |
| uguuggaagu ugaaauguga ucacagugca cucaucagag caccauugac cugcgcccag | 4495 |
| acagccuugu aagcucuugg caugagggc uucaguccua ggaggccuga aaucuuaaau | 4555 |
| gccuauggua ucaccgguggg cauguacaug ugacaacuau ucaccgugag ucacugugca | 4615 |
| uaauaccauc acugaucaca cgaccugcau cacgcaacag ccaugcucuu uacacugcag | 4675 |
| uggcugcgca gcugcaaaua uauucagca guaucauca uugucaaagg uuugcugucu | 4735 |
| uuuaaugagc augaauuaac aaugacagca uaggucucuc cagaaagaaa gcacuugaug | 4795 |
| cagaagguug caaccugaaa ccucaucagu cagcugcaua cauugugacu guacacaucc | 4855 |
| aacggaaaca ugcacacacc accccagcaa uccaagaga aaguuccuuu gggauaauaa | 4915 |
| aucacugccc gauaaagcuu ugcacacgc acagugcaau ugacagucau acuguaugua | 4975 |
| gcaaagcgca acuuuagccc gguguauuuu guugcggacu ucucuacacu guacaaaccc | 5035 |
| uugacaacuc aaccuaaggc acaaugcuac acggugaug cacaugcaaa gcuuaaacag | 5095 |
| caucagaguc agcucagcca ggucacacug ugacagcauc ucauauguug aauuaauacu | 5155 |
| gaaggcccau cugucagagu ggcaaaauug ucggucagc ugaauaacua cuggugccac | 5215 |
| ccgcaugagg uugcugcaag uucugaugaa aucuccacau acagccuua acucugacaa | 5275 |
| gcacaucaaa gcaggaggcc cucaaauugu gcggcaaaga cccaccgcag acccaaaaaa | 5335 |
| ucgcauccgu uucauauauu ugccagauac cacucugaug cuguacaccc uaaaauacac | 5395 |
| ccgaaguauc auucuucaug gguucauaua cacucuucaa aauuaaagga cggccagcuc | 5455 |
| aagcuggcuu aaugguugca gcggcccugc ugcuguuugc aaugaaugau gggugaugua | 5515 |
| caguccaagg ccucgucagc uuggcaccau ugcacuugcu guguuu | 5561 |

<210> SEQ ID NO 3
<211> LENGTH: 1036
<212> TYPE: PRT
<213> ORGANISM: Pseudochoricystis ellipsoidea

<400> SEQUENCE: 3

Met Asp Asn Gln Ser Ser Gly Thr Ser Arg Gly Met Glu Arg Arg Cys
1               5                   10                  15

Leu Thr Val Pro Gly Leu Gly Lys Gly Asn Glu Gly Phe Asp Asn Glu
            20                  25                  30

Asn Asn Asp Leu Ile Leu Tyr Val Asp Asp Val Leu Ser Val Lys Glu
        35                  40                  45

Arg Arg Tyr Ile Val Arg Asp Met Leu Gly Gln Gly Thr Phe Gly Gln
    50                  55                  60

```
Val Val Arg Cys Leu Arg Glu Asp Ser Arg Glu Val Ala Val Lys
 65                  70                  75                  80

Val Ile Lys Asn Gln Thr Ala Phe Tyr His Gln Ala Arg Val Glu Val
                 85                  90                  95

Gly Val Leu Gln Phe Leu Asn Thr Arg Gly Asp Pro Glu Asn Arg His
                100                 105                 110

His Ile Val Arg Met Arg Asp Phe Phe Leu Phe Arg Asn His Leu Cys
                115                 120                 125

Leu Val Phe Glu Leu Leu Ser Val Asn Leu Tyr Glu Leu Val Lys His
130                 135                 140

Asn Gln Phe Arg Gly Leu Ser Met Asn Leu Leu Arg Val Phe Ile Ser
145                 150                 155                 160

Gln Ile Leu Asp Ala Leu Ser Val Leu His Glu Cys Asn Ile Ile His
                165                 170                 175

Cys Asp Leu Lys Pro Glu Asn Val Leu Leu Lys Gly Leu Asp Ser Gly
                180                 185                 190

Glu Ile Lys Val Ile Asp Phe Gly Ser Ala Cys Phe Glu Asn Arg Thr
                195                 200                 205

Met Tyr Ser Tyr Ile Gln Ser Arg Phe Tyr Arg Ser Pro Glu Val Leu
210                 215                 220

Leu Gly Tyr Pro Tyr Asp Val Ala Ile Asp Met Trp Ser Leu Gly Cys
225                 230                 235                 240

Met Ala Ala Glu Leu Tyr Leu Gly Leu Pro Leu Phe Pro Gly Ala Ser
                245                 250                 255

Glu His Asp Leu Leu Val Arg Ile Val Glu Met Leu Gly Met Pro Pro
                260                 265                 270

Pro His Val Leu Ala Arg Ala Gln His Leu Arg Lys Tyr Phe Lys Arg
                275                 280                 285

Glu Glu Glu Val Leu Asn Val Gly Gly Val Pro Met Arg Arg Gln Lys
                290                 295                 300

Tyr Arg Leu Arg Thr Gln Ala Glu Phe Glu Ala Met Gln Asn Val Lys
305                 310                 315                 320

Ala Pro Ala Gly Lys Arg Tyr Phe Gln His Thr Lys Leu Pro Asp Ile
                325                 330                 335

Ile Gly Ala Tyr Pro Phe Arg Ser Gly Leu Thr Glu Ala Gln Gln Ala
                340                 345                 350

His Glu Thr Glu Arg Arg Glu Ala Phe Leu Asp Phe Leu Met Gly Val
                355                 360                 365

Leu Asp Leu Asp Pro Glu Val Arg Trp Ser Pro Gln Gln Ala Leu Gln
                370                 375                 380

His Pro Phe Leu Thr Gly Ala Arg Phe Thr Gly Pro Phe Gln Pro Pro
385                 390                 395                 400

Pro Arg Val His Val Arg Ala Arg Pro Ala Ala Pro Arg Ser Ala
                405                 410                 415

Pro Asp Gly Ser Gly Val Met Ser Pro Tyr Asn Ser Ala Leu Tyr Asn
                420                 425                 430

Ser Pro Val Ala Thr Met Leu Ala Thr Ser Pro Glu Phe His Ala Gln
                435                 440                 445

Ala His Ala Ala Ala Met Ala Ala Val Gln Ala His Phe Ser Pro Arg
                450                 455                 460

Gly Ala Gly Ala Leu Gly Ala Ser Leu Gly Ala Pro Gln Gln Gln Asn
465                 470                 475                 480
```

-continued

```
Ser Phe Glu Pro Ala Ile Ala Val Ala Ser Ala Leu Ala Ala Ala Gln
                485                 490                 495

Tyr Asn Gly Ile Gln Gln Gln Asn Gly Met Gln Gln His Thr Pro Ala
            500                 505                 510

Asp Arg Ala Gln Gln Ala Gln Tyr Gln His Ser Gly Ala Val His Ile
            515                 520                 525

Gln Gln Gln Ala Leu His Gly Met Gln Tyr Gly Ser Phe Asp Pro Met
            530                 535                 540

Tyr Ala Ser Gly His His Ser Ser Ser Gln Thr Asp Thr Pro Tyr Gly
545                 550                 555                 560

Thr Pro Tyr Gly Ser Phe Ser Gly Gly Ser Phe Ser Ser Leu Ser Ser
                565                 570                 575

Met Gln Thr Pro Pro His Ser Leu Ser Gly Tyr Ser Pro Met Thr His
            580                 585                 590

Leu His Gly Leu Pro Ser Ser Tyr His Ser Thr Pro Gly Arg Ser Gly
                595                 600                 605

Ala His Ala Gly Ser Leu Gln Gly Thr Pro Met Ala Thr Ser Tyr Asn
            610                 615                 620

Ser Tyr Ser Tyr Leu Ala Ala Ala Ala Ala Ala Ser Ala Gln Gln
625                 630                 635                 640

Ala Ala Gln Gln Pro Val Val Gly Ser Leu Glu Thr Leu Arg Ala Asn
                645                 650                 655

Ala Met Trp Asn Leu Pro His Gly Pro Ala Phe Leu Asn Gly Gln Pro
            660                 665                 670

Asn Ala Ala Tyr Leu Gly Thr Ser His Ala Arg Ile Gly Ser Gly Ala
            675                 680                 685

Phe Gly Asp Gly Met Leu Gly Ser Leu Pro Arg Glu Asn Leu Leu Gly
690                 695                 700

Thr Leu Gln Asp Ala Asp His His Gly Ala Gln Gln Ala Ala Asp Lys
705                 710                 715                 720

Arg Ala Asn Ser Gly Pro Cys Ala Ser Ala Glu Met Ala Ala Cys
                725                 730                 735

Ser Leu Gly Asn Tyr Ala Gly Asn Val Leu Pro Asp Gly Pro Ala Gln
            740                 745                 750

Gln Gln Gln Arg Leu Asp Pro Gln Gln Gln Ser Trp His Ser Phe Thr
            755                 760                 765

Gln Ser Leu Gln Gln Cys Thr Ser Pro Gln Gln Asp Arg His Ser Asn
770                 775                 780

Thr Ala Gly Ile Glu Leu Pro Pro Gly Ala Ser Asn Gly Val Ser Ser
785                 790                 795                 800

Ala Gln Gln Gly Ser Ala Ala Glu Gln Gln Gln Arg Gly Ala His Arg
                805                 810                 815

Pro Glu Gln Ala Thr Glu Arg Gln Gln Pro Asp Gln Ala Arg Leu Pro
            820                 825                 830

Pro Glu His Leu Pro Pro Lys Glu Ala Thr Ser Arg Arg Val Leu Thr
            835                 840                 845

Tyr Glu Glu His Leu Arg Glu Glu Leu Lys Ala Gln Leu Ala Glu
850                 855                 860

Arg Thr Gly Gly Glu Ala Glu Gly Thr Gly Arg Gly Ala Pro Ala
865                 870                 875                 880

Ala Ser Ala Gly Asn Gly Ala Ala Ser Leu Ser Glu Gly Arg Thr Asn
                885                 890                 895

Met Ser Arg Thr His Ser Gln Asp Val Gly Pro Thr Pro Ser Asp Trp
```

```
                900             905             910
Asp Pro Ser Tyr Ser Asp Gln Leu Leu Asp Ala Gly Trp Ala
            915             920             925
Arg Phe Pro Asp Gly Arg Ala Arg Gln Ser Ala Arg Ser Ala Leu Leu
        930             935             940
Pro Arg Phe Ala Asp Thr Ala Ala Ala Ala Thr Asp Ala Ala Gly
945             950             955             960
Gly Pro Ala Gln Pro Gln Leu Pro Gly Ser Tyr Ala Glu Ser Leu Thr
            965             970             975
Ser Pro Val Gln Pro Ser Pro Gln Gly Pro Tyr Asp Thr His Trp Leu
            980             985             990
Arg Cys Asn Gly Asp Ala Ala Leu Arg His Ala Ala Ala Asp Thr Pro
            995             1000            1005
Leu Ser Met Leu Pro Gly Ser Leu Ile Pro Lys Ala Pro Tyr Thr
        1010            1015            1020
Ser Ile Gly Phe Ala Pro Gly Lys Arg Ser Gly Cys Asn
        1025            1030            1035

<210> SEQ ID NO 4
<211> LENGTH: 83
<212> TYPE: PRT
<213> ORGANISM: Pseudochoricystis ellipsoidea

<400> SEQUENCE: 4

Ile His Cys Asp Leu Lys Pro Glu Asn Val Leu Leu Lys Gly Leu Asp
1               5                   10                  15
Ser Gly Glu Ile Lys Val Ile Asp Phe Gly Ser Ala Cys Phe Glu Asn
                20                  25                  30
Arg Thr Met Tyr Ser Tyr Ile Gln Ser Arg Phe Tyr Arg Ser Pro Glu
            35                  40                  45
Val Leu Leu Gly Tyr Pro Tyr Asp Val Ala Ile Asp Met Trp Ser Leu
        50                  55                  60
Gly Cys Met Ala Ala Glu Leu Tyr Leu Gly Leu Pro Leu Phe Pro Gly
65                  70                  75                  80
Ala Ser Glu

<210> SEQ ID NO 5
<211> LENGTH: 26
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t

<400> SEQUENCE: 5
atccactgcg acctnaarcc ngaraa                                              26

<210> SEQ ID NO 6
<211> LENGTH: 23
<212> TYPE: DNA
<213> ORGANISM: Artificial Sequence
<220> FEATURE:
<223> OTHER INFORMATION: primer
```

```
<400> SEQUENCE: 6
cagcccarrc tccacatrtc dat                                        23

<210> SEQ ID NO 7
<211> LENGTH: 23
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (9)..(9)
<223> OTHER INFORMATION: n is a, c, g, or t

<400> SEQUENCE: 7
cagcccarng accacatrtc dat                                        23
```